(12) United States Patent
Ririe et al.

(10) Patent No.: US 11,866,774 B2
(45) Date of Patent: Jan. 9, 2024

(54) HIGH DENSITY SELF-CONTAINED BIOLOGICAL ANALYSIS

(71) Applicant: BioFire Diagnostics, LLC, Salt Lake City, UT (US)

(72) Inventors: Kirk M. Ririe, Salt Lake City, UT (US); Mark Aaron Poritz, Salt Lake City, UT (US); Randy P. Rasmussen, Salt Lake City, UT (US)

(73) Assignee: BioFire Diagnostics, LLC, Salt Lake City, UT (US)

( * ) Notice: Subject to any disclaimer, the term of this patent is extended or adjusted under 35 U.S.C. 154(b) by 369 days.

(21) Appl. No.: 17/114,622

(22) Filed: Dec. 8, 2020

(65) Prior Publication Data

US 2021/0095330 A1    Apr. 1, 2021

Related U.S. Application Data

(60) Continuation of application No. 15/925,419, filed on Mar. 19, 2018, now Pat. No. 10,889,856, which is a continuation of application No. 14/801,566, filed on Jul. 16, 2015, now Pat. No. 10,053,728, which is a division of application No. 13/751,560, filed on Jan. 28, 2013, now Pat. No. 9,102,911, which is a continuation of application No. 12/515,123, filed as application No. PCT/US2007/084637 on Nov. 14, 2007, now Pat. No. 8,895,295.

(60) Provisional application No. 60/859,225, filed on Nov. 15, 2006.

(51) Int. Cl.
| | |
|---|---|
| C12Q 1/686 | (2018.01) |
| C12M 1/26 | (2006.01) |
| B01L 3/00 | (2006.01) |
| B01L 7/00 | (2006.01) |

(52) U.S. Cl.
CPC .............. *C12Q 1/686* (2013.01); *B01L 3/502* (2013.01); *B01L 3/502738* (2013.01); *B01L 7/52* (2013.01); *C12M 33/00* (2013.01); *B01L 2200/10* (2013.01); *B01L 2200/16* (2013.01); *B01L 2300/044* (2013.01); *B01L 2300/0654* (2013.01); *B01L 2300/0816* (2013.01); *B01L 2300/0864* (2013.01); *B01L 2300/0867* (2013.01); *B01L 2300/1822* (2013.01); *B01L 2400/049* (2013.01); *B01L 2400/0481* (2013.01); *B01L 2400/0655* (2013.01)

(58) Field of Classification Search
CPC ... C12Q 1/686; B01L 3/502; B01L 3/502738; B01L 7/52; B01L 2200/10; B01L 2200/16; B01L 2300/044; B01L 2300/0654; C12M 33/00
See application file for complete search history.

(56) References Cited

U.S. PATENT DOCUMENTS

| | | | |
|---|---|---|---|
| 5,229,297 A | 7/1993 | Schnipelsky et al. | |
| 5,620,869 A | 4/1997 | Woodard et al. | |
| 5,863,502 A | 1/1999 | Southgate et al. | |
| 5,876,924 A | 3/1999 | Zhang et al. | |
| 5,888,723 A | 3/1999 | Sutton et al. | |
| 6,068,751 A | 5/2000 | Neukermans | |
| 6,100,084 A | 8/2000 | Miles et al. | |
| 6,143,496 A | 11/2000 | Brown et al. | |
| 6,235,471 B1 | 5/2001 | Knapp et al. | |
| 6,251,660 B1 | 6/2001 | Muir et al. | |
| 6,300,138 B1 | 10/2001 | Gleason et al. | |
| 6,605,451 B1 | 8/2003 | Marmaro et al. | |
| 6,645,758 B1 | 11/2003 | Schnipelsky et al. | |
| 6,780,617 B2 | 8/2004 | Chen | |
| 6,960,437 B2 | 11/2005 | Enzelberger et al. | |
| 6,964,862 B2 | 11/2005 | Chen | |
| 7,198,759 B2 | 4/2007 | Bryning et al. | |
| 7,476,502 B2 | 1/2009 | Willey | |
| 8,283,155 B2 | 10/2012 | Holmes et al. | |
| 8,394,608 B2 * | 3/2013 | Ririe .................... | C12Q 1/6844 435/91.2 |
| 8,940,526 B2 | 1/2015 | Ririe et al. | |
| 9,943,848 B2 | 4/2018 | Taylor et al. | |
| 10,053,728 B2 * | 8/2018 | Ririe ...................... | C12Q 1/686 |
| 10,058,866 B2 | 8/2018 | Luoma et al. | |
| 10,533,994 B2 | 1/2020 | Holmes et al. | |
| 10,889,856 B2 * | 1/2021 | Ririe ...................... | B01L 3/502 |
| 2001/0000752 A1 | 5/2001 | Franzen | |
| 2002/0058357 A1 | 5/2002 | Chang | |
| 2002/0068357 A1 | 6/2002 | Mathies et al. | |
| 2003/0008308 A1 | 1/2003 | Enzelberger et al. | |
| 2003/0094206 A1 | 5/2003 | Gerhardt et al. | |
| 2003/0127333 A1 | 7/2003 | Lauks et al. | |
| 2004/0146869 A1 | 7/2004 | Sandell | |
| 2004/0203174 A1 | 10/2004 | Jones et al. | |

(Continued)

FOREIGN PATENT DOCUMENTS

| | | |
|---|---|---|
| DE | 10339996 A1 | 4/2005 |
| EP | 0381501 A2 | 8/1990 |

(Continued)

OTHER PUBLICATIONS

Lui et al., Anal. Chem., 76, 1824-1831 (Year: 2004).*
Coiras et al., Journal of Medical Virology 72: 484-495, (Year: 2004).
Adler et al. "A real-time immuno-PCR assay for routine ultrasensitive quantification of proteins" *Biochemical and Biophysical Research Communications* 308:240-250 (2003).
Adler et al. "Detection of Rotavirus from stool samples using a standardized immuno-PCR ("*imperacer*") method with end-point and real-time detection" *Biochemical and Biophysical Research Communications* 333:1289-1294 (2005).
Adler, Michael "Immuno-PCR as a Clinical Laboratory Tool" *Advances in Clinical Chemistry* 39:239-292 (2005).

(Continued)

*Primary Examiner* — Cynthia B Wilder
(74) *Attorney, Agent, or Firm* — Myers Bigel, P.A.

(57) ABSTRACT

Devices, containers, and methods are provided for performing biological analysis in a closed environment. Illustrative biological analyses include high density nucleic acid amplification and detection and immuno-PCR.

10 Claims, 15 Drawing Sheets

(56) References Cited

U.S. PATENT DOCUMENTS

| | | |
|---|---|---|
| 2004/0209331 A1 | 10/2004 | Ririe |
| 2005/0145496 A1 | 7/2005 | Goodsaid et al. |
| 2005/0180891 A1 | 8/2005 | Webster et al. |
| 2005/0194316 A1 | 9/2005 | Pourahmadi et al. |
| 2005/0250199 A1 | 11/2005 | Anderson et al. |
| 2005/0252773 A1 | 11/2005 | McBride et al. |
| 2005/0277125 A1 | 12/2005 | Benn et al. |
| 2006/0088931 A1 | 4/2006 | Ririe |
| 2006/0177844 A1 | 8/2006 | Ching et al. |
| 2006/0216812 A1 | 9/2006 | Okada et al. |
| 2008/0057572 A1 | 3/2008 | Petersen et al. |
| 2010/0056383 A1 | 3/2010 | Ririe et al. |
| 2010/0068706 A1 | 3/2010 | Pourahmadi et al. |
| 2010/0105029 A1* | 4/2010 | Ririe .................... C12Q 1/686 435/6.12 |
| 2011/0076674 A1 | 3/2011 | Blaschke-Bonkowsky et al. |
| 2013/0137172 A1 | 5/2013 | Ririe et al. |
| 2014/0234845 A1 | 8/2014 | Poritz et al. |
| 2018/0326424 A1 | 11/2018 | Ririe et al. |

FOREIGN PATENT DOCUMENTS

| | | |
|---|---|---|
| EP | 0402994 A2 | 12/1990 |
| EP | 0 572 057 A1 | 12/1993 |
| FR | 2 760 838 A1 | 9/1998 |
| WO | 9840466 A1 | 9/1998 |
| WO | WO 03/031929 A2 | 4/2003 |
| WO | 2004004904 A2 | 1/2004 |
| WO | WO 2005/107938 A2 | 11/2005 |
| WO | WO 2006/047777 A2 | 5/2006 |

OTHER PUBLICATIONS

Allen et al. "An immuno-PCR method for detecting *Bacillus thuringiensis* Cry1Ac toxin" Journal of Immunological Methods 308:109-115 (2006).
Barletta et al. "Lowering the Detection Limits of HIV-1 Viral Load Using Real-Time Immuno-PCR for HIV-1 p24 Antigen" *American Journal of Clinical Pathology* 122:20-27 (2004).
Barletta et al. "Detection of ultra-low levels of pathologic prion protein in scrapie infected hamster brain homogenates using real-time immuno-PCR" *Journal of Virological Methods* 127:154-164 (2005).
Chao et al. "A highly sensitive immuno-polymerase chain reaction assay for *Clostridium botulinum* neurotoxin type A" *Toxicon* 43:27-34 (2004).
Dobrowolski et al. "Validation of Dye-Binding/High-Resolution Thermal Denaturation for the Identification of Mutations in the SLC22A5 Gene" *Human Mutation* 25:306-313 (2005).
Elnifro et al. "Multiplex PCR: Optimization and Application in Diagnostic Virology" *Clinical Microbiology Reviews* 13(4):559-570 (2000).
Elnifro et al. "Multiplex Polymerase Chain Reaction for Diagnosis of Viral and Chlamydial Keratoconjunctivitis" *Investigative Ophthalmology & Visual Science* 41(7):1818-1822 (2000).
Extended European Search Report corresponding to European Patent Application No. 07874275.6 (6 pages) (dated Mar. 15, 2013).
Findlay et al. "Automated Closed-Vessel System for in Vitro Diagnostics Based on Polymerase Chain Reaction" *Clinical Chemistry* 39(9):1927-1933 (1993).
Giaever et al. "Genomic profiling of drug sensitivities via induced haploinsufficiency" *Nature Genetics* 21:278-283 (1999).
Gundry et al. "Amplicon Melting Analysis with Labeled Primers: A Closed-Tube Method for Differentiating Homozygotes and Heterozygotes" *Clinical Chemistry* 49(3):396-406 (2003).
Hendrickson et al. "High sensitivity multianalyte immunoassay using covalent DNA-labeled antibodies and polymerase chain reaction" *Nucleic Acids Research* 23(3):522-529 (1995).
Hujer et al. "Analysis of Antibiotic Resistance Genes in Multidrug-Resistant *Acinetobacter* sp. Isolates from Military and Civilian Patients Treated at the Walter Reed Army Medical Center" *Antimicrobial Agents and Chemotherapy* 50(12):4114-4123 (2006).
International Preliminary Report on Patentability corresponding to International Patent Application No. PCT/US2007/084637 (15 pages) (dated May 19, 2009).
International Search Report and the Written Opinion of the International Searching Authority corresponding to International Patent Application No. PCT/US2007/084637 (8 pages) (dated Nov. 3, 2008).
Joerger et al. "Analyte Detection with DNA-Labeled Antibodies and Polymerase Chain Reaction" *Clinical Chemistry* 41(9):1371-1377 (1995).
Liang et al. "A highly sensitive immuno-PCR assay for detecting Group A *Streptococcus*" *Journal of Immunological Methods* 279:101-110 (2003).
Lind et al. "Development and evaluation of three real-time immuno-PCR assemblages for quantification of PSA" *Journal of Immunological Methods* 304:107-116 (2005).
McKie et al. "A quantitative immuno-PCR assay for the detection of mumps-specific IgG" *Journal of Immunological Methods* 270:135-141 (2002).
McKinney et al. "Rapid, comprehensive screening of the human medium chain acyl-CoA dehydrogenase gene" *Molecular Genetics and Metabolism* 82:112-120 (2004).
Niemeyer et al. "Immuno-PCR: high sensitivity detection of proteins by nucleic acid amplification" *Trends in Biotechnology* 23(4):208-216 (2005).
Rubio et al. "Semi-Nested, Multiplex Polymerase Chain Reaction for Detection of Human Malaria Parasites and Evidence of *Plasmodium vivax* Infection in Equatorial Guinea" *The American Journal of Tropical Medicine and Hygiene* 60(2):183-187 (1999).
Sanchez et al. "A multiplex assay with 52 single nucleotide polymorphisms for human identification" *Electrophoresis* 27:1713-1724 (2006).
Sano et al. "Immuno-PCR: Very Sensitive Antigen Detection by Means of Specific Antibody-DNA Conjugates" *Science* 258(5079):120-122 (1992).
Schiavo et al. "Comparison of Fluorometric Detection Methods for Quantitative Polymerase Chain Reaction (PCR)" *Journal of Immunoassay & Immunochemistry* 26:1-12 (2005).
Science Blog "Hand-portable device detects biological agents" (2 pages) (Mar. 11, 2003).
Winzeler et al. "Functional Characterization of the *S. cerevisiae* Genome by Gene Deletion and Parallel Analysis" *Science* 285:901-906 (1999).
Wittwer et al. "Minimizing the Time Required for DNA Amplification by Efficient Heat Transfer to Small Samples" *Analytical Biochemistry* 186:328-331 (1990).
Wittwer et al. "Rapid Cycle DNA Amplification: Time and Temperature Optimization" *BioTechniques* 10(1):76-83 (1991).
Wittwer et al. "Continuous Fluorescence Monitoring of Rapid Cycle DNA Amplification" *BioTechniques* 22:130-138 (1997).
Wittwer et al. "The LightCycler™: A Microvolume Multisample Fluorimeter with Rapid Temperature Control" *BioTechniques* 22:176-181 (1997).
Wittwer et al. "High-Resolution Genotyping by Amplicon Melting Analysis Using LCGreen" *Clinical Chemistry* 49(6):853-860 (2003).
Wu et al. "Detection of *Clostridium botulinum* neurotoxin type A using immuno-PCR" *Letters in Applied Microbiology* 32:321-325 (2001).
Zhou et al. "Closed-Tube Genotyping with Unlabeled Oligonucleotide Probes and a Saturating DNA Dye" *Clinical Chemistry* 50(8):1328-1335 (2004).
Bolvin , et al., "Multiplex Real-Time PCR Assay for Detection of Influenza and Human Respiratory Syncytial Viruses", Journal of Clinical Microbiology vol. 42, No. 1, 2004, 45-51.
Dong , et al., "A Miniature Piezoelectric Ultrasonic Motor Based on Circular Bending Vibration Mode", IEEE/ASME Transactions on Mechatronics vol. 5, No. 4, 2000, 325-330.
Kim , et al., ""Cell lysis on a microfluidic CD (compact disc)" The Royal Society of Chemistry—Lab Chip 4(5):516-522 (2004)".

(56) References Cited

OTHER PUBLICATIONS

Oster, et al., ""Polyvinyl-alcohol-based magnetic beads for rapid and efficient separation of specific or unspecific nucleic acid sequences" Journal of Magnetism and Magnetic Materials 225:145-150 (2001)".
Taylor, et al., ""Lysing Bacterial Spores by Sonication through a Flexible Interface in a Microfluidic System" Anal Chem 73:492-496 (2001)".
Widjojoatmodjo, et al., ""Evaluation of the Magnetic Immuno PCR Assay for Rapid Detection of *Salmonella*" European Journal of Microbiology and Infectious Diseases, 10(11):935-938 (1991)".
Yeh, et al., ""Quantification and genotyping of hepatitis B virus in a single reaction by real-time PCR and melting curve analysis" J. of Hepatology 41:659-666 (2004)".

* cited by examiner

HIGH DENSITY SELF-CONTAINED BIOLOGICAL ANALYSIS

STATEMENT OF PRIORITY

This application is a continuation of, and claims priority to, U.S. application Ser. No. 15/925,419, filed Mar. 19, 2018, which is a continuation of, and claims priority to, U.S. application Ser. No. 14/801,566, filed Jul. 16, 2015, and issued as U.S. Pat. No. 10,053,728 on Aug. 21, 2018, which is a divisional of, and claims priority to, U.S. application Ser. No. 13/751,560, filed Jan. 28, 2013, and issued as U.S. Pat. No. 9,102,911 on Aug. 11, 2015, which is a continuation of, and claims priority to, U.S. application Ser. No. 12/515,123, filed May 15, 2009 and issued as U.S. Pat. No. 8,895,295 on Nov. 25, 2014, which is a national stage application of International Application Serial No. PCT/US07/84637, filed Nov. 14, 2007, which claims priority to U.S. Provisional Application Ser. No. 60/859,225, filed on Nov. 15, 2006, the entire disclosures of each of which are incorporated herein by reference.

GOVERNMENT INTEREST

This invention was made with government support under Grant Nos. U01 AI061611 and R43 AI063695 awarded by National Institutes of Health. The government has certain rights in the invention.

BACKGROUND OF THE INVENTION

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. A challenge to using PCR as a primary means of diagnosis is the variety of possible causative organisms and the low levels of organism present in some pathological specimens. It is often impractical to run large panels of PCR assays, one for each possible causative organism, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. However, this further handling can be expensive and may lead to contamination or other problems.

Similarly, immuno-PCR ("iPCR") has the potential for sensitive detection of a wide variety of antigens. However, because traditional ELISA techniques have been applied to iPCR, iPCR often suffers from contamination issues that are problematic using a PCR-based detection method.

The present invention addresses various issues of contamination in biological analysis.

SUMMARY OF THE INVENTION

Accordingly, a rapid, sensitive assay that simultaneously assays for multiple biological substances, including organisms, is provided. The self-contained system illustratively employs an inexpensive disposable plastic pouch in a self-contained format, allowing for nested PCR and other means to identify bio-molecules, illustratively while minimizing contamination and providing for robust amplification.

Thus, in one aspect of the present invention a container for performing two-stage amplification on a sample in a closed system is provided, the container comprising a first-stage reaction zone comprising a first-stage reaction blister configured for first-stage amplification of the sample, an additional reservoir fluidly connected to the first-stage reaction blister, the additional reservoir configured for providing additional fluids to the sample, and a second-stage reaction zone fluidly connected to the first-stage reaction zone, the second-stage reaction zone comprising a plurality of second-stage reaction chambers, each second-stage reaction chamber comprising a pair of primers configured for further amplification of the sample. In one illustrative example, the first-stage reaction zone is a first-stage PCR amplification zone. In another illustrative example, the first stage reaction zone is an antigen-binding zone for immuno-PCR, in which antigens present in the sample are recognized and associated with a particular nucleic acid segment and the second stage reaction zone is a nucleic acid amplification zone. In yet another illustrative example, the container further comprises a cell lysis zone comprising particles for lysing cells or spores located in the sample, and a nucleic acid preparation zone comprising components for purifying nucleic acids. Illustratively, the blisters comprise a flexible material, such that pressure provided on an individual blister collapses the blister, forcing the contents from the blister.

In another aspect of the present invention, a container is provided comprising a flexible portion having a plurality of blisters fluidly connected via a plurality of channels, and a plurality of reservoirs, each reservoir containing a reaction component, and each reservoir fluidly connected to at least one of the plurality of blisters, and a sealable port configured for receiving the sample the sealable port fluidly connected to one of the plurality of blisters. In one illustrative embodiment, the reaction components are in dried form, and the container further comprises a second sealable port fluidly connected to each of the plurality of reservoirs, the port configured for receiving water to rehydrate the reaction components.

In a further aspect of the present invention, a method for lysing cells in a sample is provided, the method comprising providing a flexible container comprising a cell lysis blister, introducing cells into the cell lysis blister, and applying force to the blister to move the particles and sample to generate high velocity impacts resulting in a lysate.

In yet another aspect of the present invention, a device for analyzing a sample for the presence of nucleic acids is provided, the device configured to receive a container of the present invention therein, a plurality of actuators positioned corresponding to various blisters of the container, each actuator configured to apply pressure to the corresponding blister of the container, a first heater/cooler device configured for thermal cycling the contents of one of the blisters, and a second heater/cooler device for thermal cycling the second-stage chamber.

In still another aspect of the present invention, methods are provided. In one illustrative method, nucleic acids are amplified. In another illustrative method, antigens are detected using immuno-PCR.

In an addition aspect of the present invention a high density reaction zone is provided, comprising a channel, a plurality of high density reaction wells fluidly connected to the channel, each high density reaction well comprising one or more reagents, and a barrier layer that minimizes cross-contamination between high density reaction wells upon introduction of the sample to the high density reaction zone. The barrier layer may be a physical layer, illustratively a pierced layer that minimizes flow through the piercings absent a force to move the sample through the piercings. Alternatively, the barrier may be a chemical barrier that keeps the reagents in the wells until the wells can be sealed.

Additional features of the present invention will become apparent to those skilled in the art upon consideration of the following detailed description of preferred embodiments exemplifying the best mode of carrying out the invention as presently perceived.

DETAILED DESCRIPTION

The self-contained nucleic acid analysis pouches described herein may be used to assay a sample for the presence of various biological substances, illustratively antigens and nucleic acid sequences, illustratively in a single closed system. In one embodiment, the pouch is used to assay for multiple pathogens. Illustratively, various steps may be performed in the optionally disposable pouch, including nucleic acid preparation, primary large volume multiplex PCR, dilution of primary amplification product, and secondary PCR, culminating with real-time detection and/or post-amplification analysis such as melting-curve analysis. It is understood, however, that pathogen detection is one exemplary use and the pouches may be used for other nucleic acid analysis or detection of other substances, including but not limited to peptides, toxins, and small molecules. Further, it is understood that while the various steps may be performed in pouches of the present invention, one or more of the steps may be omitted for certain uses, and the pouch configuration may be altered accordingly.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAM); target based-helicase dependent amplification (HDA); transcription-mediated amplification (TMA), and the like. Therefore, when the term PCR is used, it should be understood to include other alternative amplification methods. It is understood that protocols may need to be adjusted accordingly.

Figure 1:
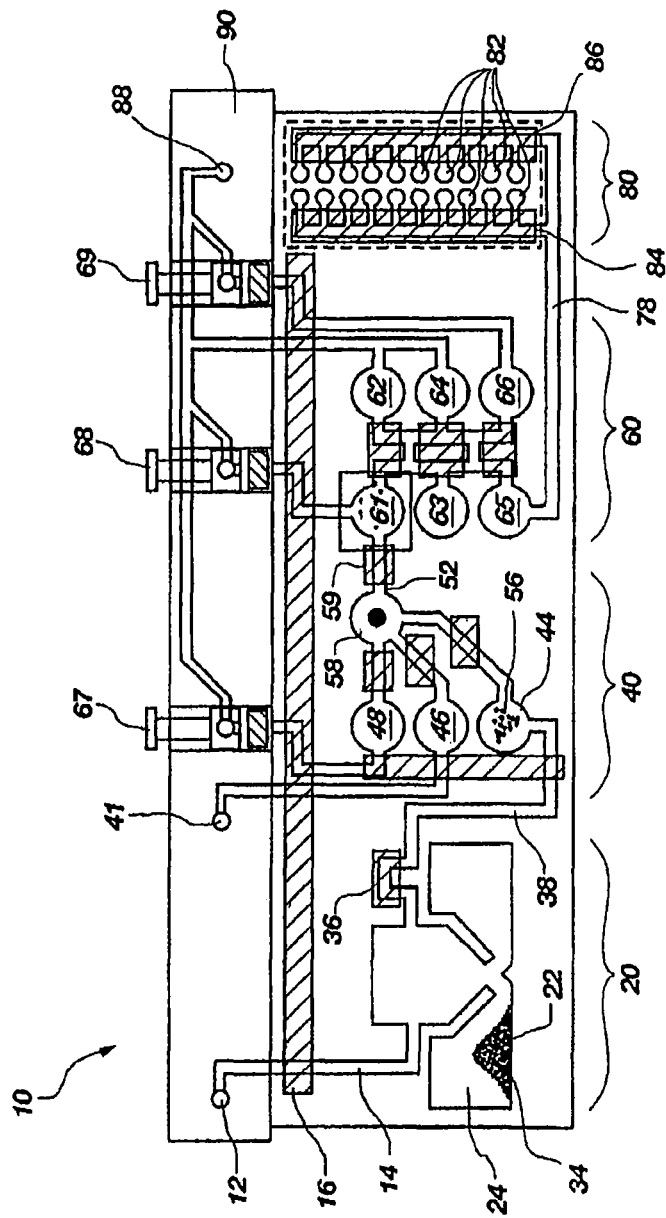
FIG. 1 shows a flexible pouch according to one embodiment of this invention.

FIG. 1 shows an illustrative self-contained nucleic acid analysis pouch 10. Pouch 10 has a cell lysis zone 20, a nucleic acid preparation zone 40, a first-stage amplification zone 60, and a second-stage amplification zone 80. A sample containing nucleic acid is introduced into the pouch 10 via sample injection port 12. Pouch 10 comprises a variety of channels and blisters of various sizes and is arranged such that the sample flows through the system. The sample passes through the various zones and is processed accordingly.

Sample processing occurs in various blisters located within pouch 10. Various channels are provided to move the sample within and between processing zones, while other channels are provided to deliver fluids and reagents to the sample or to remove such fluids and reagents from the sample. Liquid within pouch 10 illustratively is moved between blisters by pressure, illustratively pneumatic pressure, as described below, although other methods of moving material within the pouch are contemplated.

While other containers may be used, illustratively, pouch 10 is formed of two layers of a flexible plastic film or other flexible material such as polyester, polyethylene terephthalate (PET), polycarbonate, polypropylene, polymethylmethacrylate, and mixtures thereof that can be made by any process known in the art, including extrusion, plasma deposition, and lamination. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by trying different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in the blisters 82 of the second stage amplification zone 80 of pouch 10, then one or both layers at blisters 82 would be left without the foil. In the example of PCR, film laminates composed of polyester (Mylar, Dupont, Wilmington DE) of about 0.0048 inch (0.1219 mm) thick and polypropylene films of 0.001-0.003 inch (0.025-0.076 mm) thick perform well. Illustratively, pouch 10 is made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pneumatic pressure, the pouch material illustratively is flexible enough to allow the pneumatic pressure to have the desired effect. The term "flexible" is herein used to describe a physical characteristic of the material of pouch. The term "flexible" is herein defined as readily deformable by the levels of pneumatic pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 10 may be made of a rigid material or may be reinforced with a rigid material.

Illustratively, a plastic film is used for pouch 10. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton WI), illustratively regulated at an operating temperature of 195° C., the pneumatic press works like a printing press, melting the sealing surfaces of plastic film only where the die contacts the film. Various components, such as PCR primers (illustratively spotted onto the film and dried), antigen binding substrates, magnetic beads, and zirconium silicate beads may be sealed inside various blisters as the pouch 10 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction is hydrated by an aqueous sample. If the aqueous sample has been heated prior to hydration, this creates the conditions for a true hot-start PCR and reduces or eliminates the need for expensive chemical hot-start components. This separate spotting is discussed further below, with respect to FIG. 5b, but it is understood that such spotting may be used with any of the embodiments discussed herein.

Figure 2:
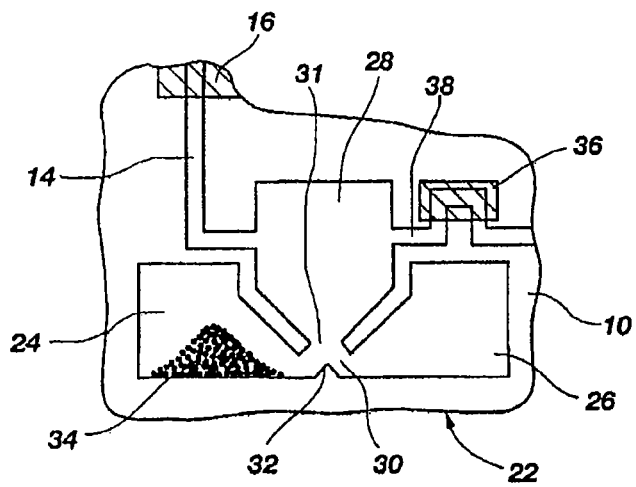
FIG. 2 shows an embodiment of the cell lysis zone of the flexible pouch according to FIG. 1.
Figure 2A:
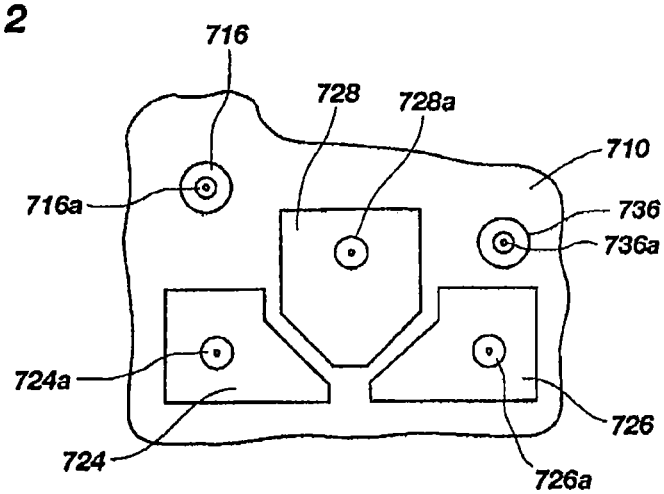
FIG. 2a shows an embodiment of a portion of a bladder corresponding to the cell lysis zone shown in FIG. 2.

When pneumatic pressure is used to move materials within pouch 10, in one embodiment a "bladder" may be employed. The bladder assembly 710, a portion of which is shown in FIG. 2a, may be manufactured in a process similar to that of making the pouch, but individual blisters in the bladder assembly 710 include pneumatic fittings (illustratively fitting 724a) allowing individual bladders within the bladder assembly 710 to be pressurized by a compressed gas source. Because the bladder assembly is subjected to compressed gas and may be used multiple times, the bladder assembly may be made from tougher or thicker material than the pouch. Alternatively, bladders may be formed from a series of plates fastened together with gaskets, seals, valves, and pistons. Other arrangements are within the scope of this invention.

When pouch 10 is placed within the instrument, the pneumatic bladder assembly 710 is pressed against one face of the pouch 10, so that if a particular bladder is inflated, the pressure will force the liquid out of the corresponding blister in the pouch 10. In addition to pneumatic bladders corresponding to many of the blisters of pouch 10, the bladder assembly may have additional pneumatic actuators, such as bladders or pneumatically-driven pistons, corresponding to various channels of pouch 10. When activated, these additional pneumatic actuators form pinch valves to pinch off and close the corresponding channels. To confine liquid within a particular blister of pouch 10, the pinch valve pneumatic actuators are inflated over the channels leading to and from the blister, such that the actuators function as pinch valves to pinch the channels shut. Illustratively, to mix two volumes of liquid in different blisters, the pinch valve pneumatic actuator sealing the connecting channel is depressurized, and the pneumatic bladders over the blisters are alternately pressurized, forcing the liquid back and forth through the channel connecting the blisters to mix the liquid therein. The pinch valve pneumatic actuators may be of various shapes and sizes and may be configured to pinch off more than one channel at a time. Such an illustrative pinch valve is illustrated in FIG. 1 as pinch valve 16, which may be used to close all injection ports. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch could be transitioned in one or two dimensions such that a small number of actuators could be used for several of the processing stations including sample disruption, nucleic-acid capture, first and second-stage PCR, and other applications of the pouch such as immunoassay and immuno-PCR. Rollers acting on channels and blisters could prove particularly useful in a configuration in which the pouch is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

With reference to FIG. 1, an illustrative sample pouch 10 configured for nucleic acid extraction and multiplex PCR is provided. The sample enters pouch 10 via sample injection port 12 in fitment 90. Injector port 12 may be a frangible seal, a one-way valve, or other entry port. Vacuum from inside pouch 10 may be used to draw the sample into pouch 10, a syringe or other pressure may be used to force the sample into pouch 10, or other means of introducing the sample into pouch 10 via injector port 12 may be used. The sample travels via channel 14 to the three-lobed blister 22 of the cell lysis zone 20, wherein cells in the sample are lysed. Once the sample enters three-lobed blister 22, pinch valve 16 is closed. Along with pinch valve 36, which may have been already closed, the closure of pinch valve 16 seals the sample in three-lobed blister 22. It is understood that cell lysis may not be necessary with every sample. For such samples, the cell lysis zone may be omitted or the sample may be moved directly to the next zone. However, with many samples, cell lysis is needed. In one embodiment, bead-milling is used to lyse the cells.

Bead-milling, by shaking or vortexing the sample in the presence of lysing particles such as zirconium silicate (ZS) beads 34, is an effective method to form a lysate. It is understood that, as used herein, terms such as "lyse," "lysing," and "lysate" are not limited to rupturing cells, but that such terms include disruption of non-cellular particles, such as viruses. FIG. 2 displays one embodiment of a cell lysis zone 20, where convergent flow creates high velocity bead impacts, to create lysate. Illustratively, the two lower lobes 24, 26 of three-lobed blister 22 are connected via channel 30, and the upper lobe 28 is connected to the lower lobes 24, 26 at the opposing side 31 of channel 30. FIG. 2a shows a counterpart portion of the bladder assembly 710 that would be in contact with the cell lysis zone 20 of the pouch 10. When pouch 10 is placed in an instrument, adjacent each lobe 24, 26, 28 on pouch 10 is a corresponding pneumatic bladder 724, 726, 728 in the bladder assembly 710. It is understood that the term "adjacent," when referring to the relationship between a blister or channel in a pouch and its corresponding pneumatic actuator, refers to the relationship between the blister or channel and the corresponding pneumatic actuator when the pouch is placed into the instrument. In one embodiment, the pneumatic fittings 724a, 726a of the two lower pneumatic bladders 724, 726 adjacent lower lobes 24, 26 are plumbed together. The pneumatic fittings 724a, 726a and the pneumatic fitting 728a of upper pneumatic bladder 728 adjacent upper lobe 28 are plumbed to the opposing side of an electrically actuated valve configured to drive a double-acting pneumatic cylinder. Thus configured, pressure is alternated between the upper pneumatic bladder 728 and the two lower pneumatic bladders 724, 726. When the valve is switched back and forth, liquid in pouch 10 is driven between the lower lobes 24, 26 and the upper lobe 28 through a narrow nexus 32 in channel 30. As the two lower lobes 24, 26 are pressurized at the same time, the flow converges and shoots into the upper lobe 28. Depending on the geometry of the lobes, the collision velocity of beads 34 at the nexus 32 may be at least about 12 m/sec, providing high-impact collisions resulting in lysis. The illustrative three-lobed system allows for good cell disruption and structural robustness, while minimizing size and pneumatic gas consumption. While ZS beads are used as the lysing particles, it is understood that this choice is illustrative only, and that other materials and particles of other shapes may be used. It is also understood that other configurations for cell lysis zone 20 are within the scope of this invention.

While a three-lobed blister is used for cell lysis, it is understood that other multi-lobed configurations are within the scope of this invention. For instance, a four-lobed blister, illustratively in a cloverleaf pattern, could be used, wherein the opposite blisters are pressurized at the same time, forcing the lysing particles toward each other, and then angling off to the other two lobes, which then may be pressurized together. Such a four-lobed blister would have the advantage of having high-velocity impacts in both directions. Further, it is contemplated that single-lobed blisters may be used, wherein the lysing particles are moved rapidly from one portion of the single-lobed blister to the other. For example, pneumatic actuators may be used to close off areas of the single-lobed blister, temporarily forming a multi-lobed blister in the remaining areas. Other actuation methods may also be used such as motor, pneumatic, hydraulic, or electromagnetically-driven paddles acting on the lobes of the device. Rollers or rotary paddles can be used to drive fluid together at the nexus 32 of FIG. 2, illustratively if a recirculation means is provided between the upper and lower lobes and the actuator provides peristaltic pumping action. Other configurations are within the scope of this invention.

Figure 2B:
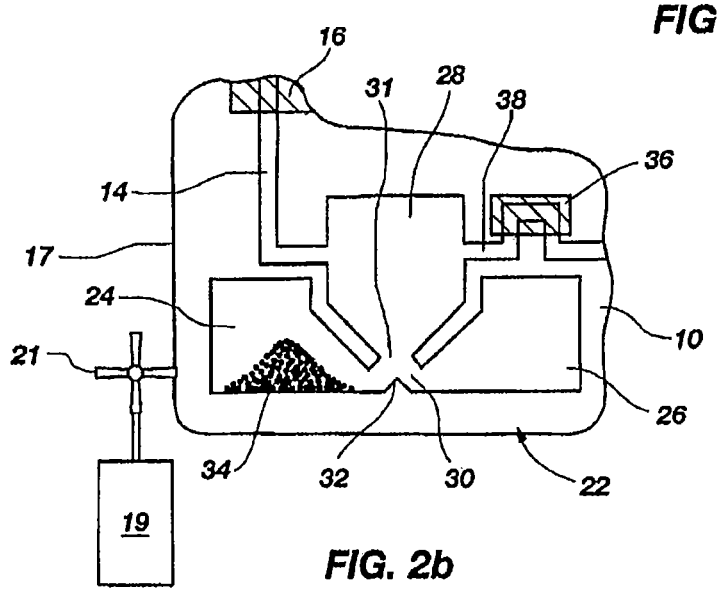
FIG. 2b shows an embodiment of the cell lysis zone of the flexible pouch according to FIG. 1 having an alternative vortexing mechanism.
Figure 15:
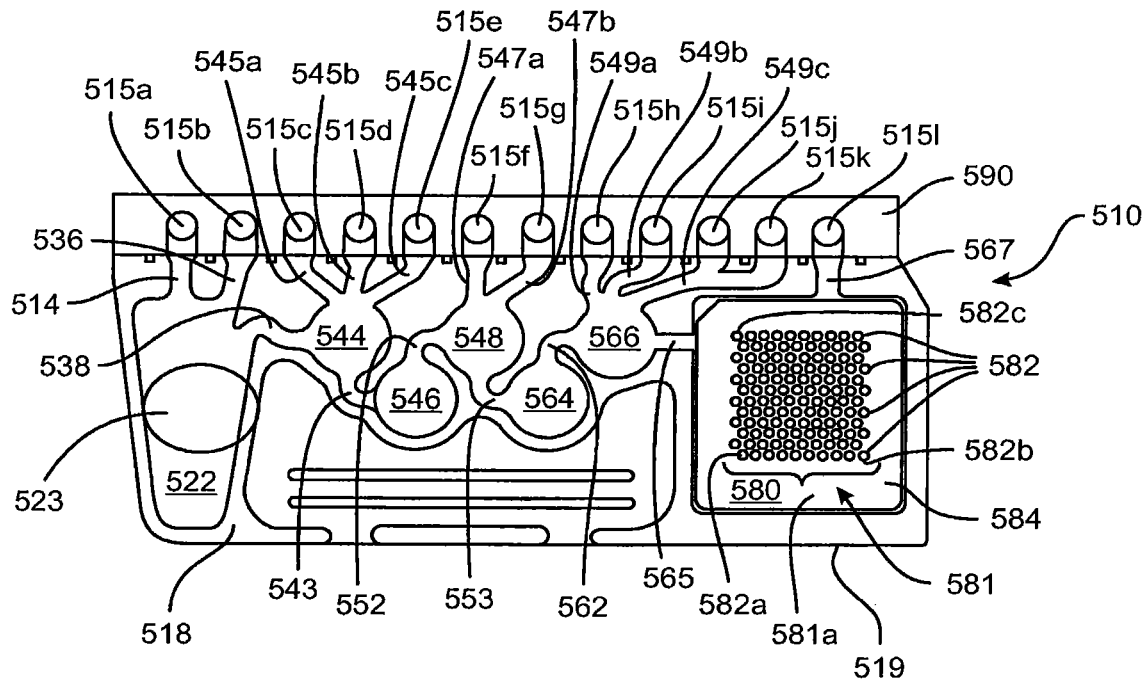
FIG. 15 is similar to FIG. 6, except showing a pouch having a second-stage high density array.
Figure 15A:
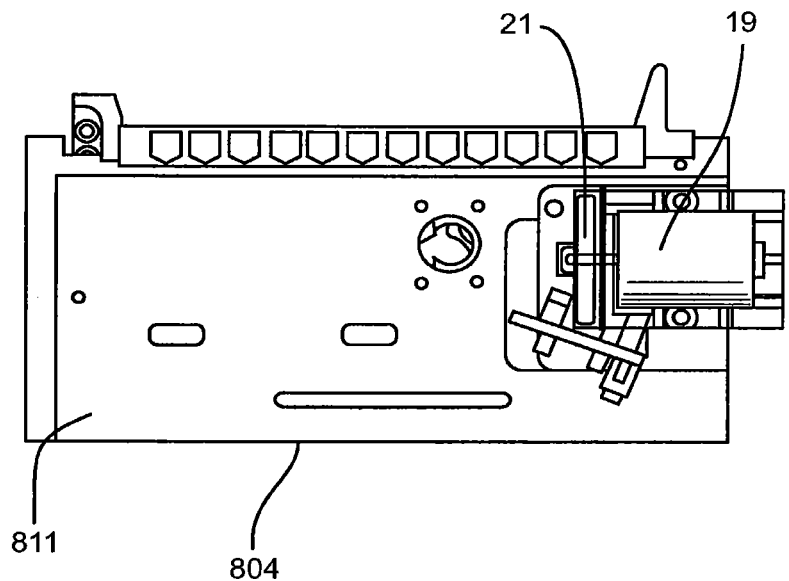
FIG. 15a shows a modification of a component of the instrument of FIG. 8. A support member has been provided with a motor configured for use with the pouch of FIG. 15.

It may also be possible to move the sample and lysing particles quickly enough to effect lysis within a single-lobed lysis blister without temporarily forming a multi-lobed blister. In one such alternative embodiment, as shown in FIG. 2b, vortexing may be achieved by impacting the pouch with rotating blades or paddles 21 attached to an electric motor 19. The blades 21 may impact the pouch at the lysis blister or may impact the pouch near the lysis blister, illustratively at an edge 17 adjacent the lysis blister. In such an embodiment, the lysis blister may comprise one or more blisters. FIG. 15 shows an embodiment comprising one such lysis blister 522. FIG. 15a shows a bead beating motor 19, comprising blades 21, that may be mounted on a first side 811 of second support member 804, of instrument 800 shown in FIG. 8. It is understood, however, that motor 19 may be mounted on first support member 802 or on other structure of instrument 800.

FIG. 2a also shows pneumatic bladder 716 with pneumatic fitting 716a, and pneumatic bladder 736 with pneumatic fitting 736a. When the pouch 10 is placed in contact with bladder assembly 710, bladder 716 lines up with channel 12 to complete pinch valve 16. Similarly, bladder 736 lines up with channel 38 to complete pinch valve 36. Operation of pneumatic bladders 716 and 736 allow pinch valves 16 and 36 to be opened and closed. While only the portion of bladder assembly 710 adjacent the cell lysis zone is shown, it is understood that bladder assembly 710 would be provided with similar arrangements of pneumatic blisters to control the movement of fluids throughout the remaining zones of pouch 10.

Other prior art instruments teach PCR within a sealed flexible container. See, e.g., U.S. Pat. Nos. 6,645,758 and 6,780,617, and co-pending U.S. patent application Ser. No. 10/478,453, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. However, it is understood that the pouch contents could be removed for further testing.

Figure 3:
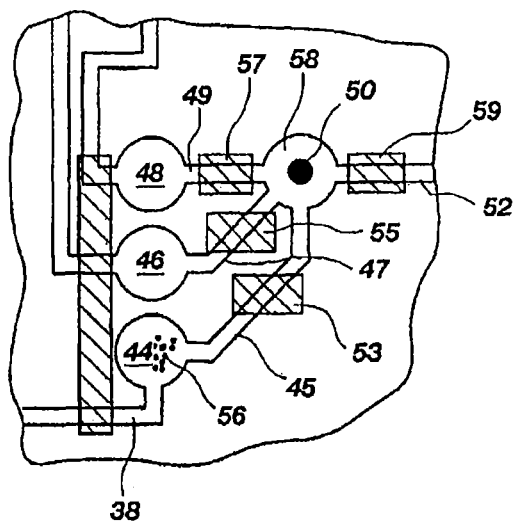
FIG. 3 shows an embodiment of the nucleic acid preparation zone of the flexible pouch according to FIG. 1.

Once the cells are lysed, pinch valve 36 is opened and the lysate is moved through channel 38 to the nucleic acid preparation zone 40, as best seen in FIG. 3, after which, pinch valve 36 is closed, sealing the sample in nucleic acid preparation zone 40. In the embodiment illustrated in FIG. 3, purification of nucleic acids takes the bead-milled material and uses affinity binding to silica-based magnetic-beads 56, washing the beads with ethanol, and eluting the nucleic acids with water or other fluid, to purify the nucleic acid from the cell lysate. The individual components needed for nucleic acid extraction illustratively reside in blisters 44, 46, 48, which are connected by channels 45, 47, 49 to allow reagent mixing. The lysate enters blister 44 from channel 38. Blister 44 may be provided with magnetic beads 56 and a suitable binding buffer, illustratively a high-salt buffer such as that of 1-2-3™ Sample Preparation Kit (Idaho Technology, Salt Lake City, UT) or either or both of these components may be provided subsequently through one or more channels connected to blister 44. The nucleic acids are captured on beads 56, pinch valve 53 is then opened, and the lysate and beads 56 may be mixed by gentle pressure alternately on blisters 44 and 58 and then moved to blister 58 via pneumatic pressure illustratively provided by a corresponding pneumatic bladder on bladder assembly 710. The magnetic beads 56 are captured in blister 58 by a retractable magnet 50, which is located in the instrument adjacent blister 58, and waste may be moved to a waste reservoir or may be returned to blister 44 by applying pressure to blister 58. Pinch valve 53 is then closed. The magnetic beads 56 are washed with ethanol, isopropanol, or other organic or inorganic wash solution provided from blister 46, upon release of pinch valve 55. Optionally, magnet 50 may be retracted allowing the beads to be washed by providing alternate pressure on blisters 46 and 58. The beads 56 are once again captured in blister 58 by magnet 50, and the non-nucleic acid portion of the lysate is washed from the beads 56 and may be moved back to blister 46 and secured by pinch valve 55 or may be washed away via another channel to a waste reservoir. Once the magnetic beads are washed, pinch valve 57 is opened, releasing water (illustratively buffered water) or another nucleic acid eluant from blister 48. Once again, the magnet 50 may be retracted to allow maximum mixing of water and beads 56, illustratively by providing alternate pressure on blisters 48 and 58. The magnet 50 is once again deployed to collect beads 56. Pinch valve 59 is released and the eluted nucleic acid is moved via channel 52 to first-stage amplification zone 60. Pinch valve 59 is then closed, thus securing the sample in first-stage amplification zone 60.

It is understood that the configuration for the nucleic acid preparation zone 40, as shown in FIG. 3 and described above, is illustrative only, and that various other configurations are possible within the scope of the present disclosure.

The ethanol, water, and other fluids used herein may be provided to the blisters in various ways. The fluids may be stored in the blisters, the necks of which may be pinched off by various pinch valves or frangible portions that may be opened at the proper time in the sample preparation sequence. Alternatively, fluid may be stored in reservoirs in the pouch as shown pouch 110 in FIG. 5, or in the fitment as discussed with respect to pouch 210 of FIG. 6, and moved via channels, as necessary. In still another embodiment, the fluids may be introduced from an external source, as shown in FIG. 1, especially with respect to ethanol injection ports 41, 88 and plungers 67, 68, 69. Illustratively, plungers 67, 68, 69 may inserted into fitment 90, illustratively of a more rigid material, and may provide a measured volume of fluid upon activation of the plunger, as in U.S. patent application Ser. No. 10/512,255, herein incorporated by reference. The measured volume may be the same or different for each of the plungers. Finally, in yet another embodiment, the pouch may be provided with a measured volume of the fluid that is stored in one or more blisters, wherein the fluid is contained within the blister, illustratively provided in a small sealed pouch within the blister, effectively forming a blister within the blister. At the appropriate time, the sealed pouch may then be ruptured, illustratively by pneumatic pressure, thereby releasing the fluid into the blister of the pouch. The instrument may also be configured the provide some or all of the reagents directly through liquid contacts between the instrument and the fitment or pouch material provided that the passage of fluid is tightly regulated by a one-way valve to prevent the instrument from becoming contaminated during a run. Further, it will often be desirable for the pouch or its fitment to be sealed after operation to prohibit contaminating DNA to escape from the pouch. Various means are known to provide reagents on demand such as syringe pumps, and to make temporary fluid contact with the fitment or pouch, such as barbed fittings or o-ring seals. It is understood that any of these methods of introducing fluids to the appropriate blister may be used with any of the embodiments of the pouch as discussed herein, as may be dictated by the needs of a particular application.

As discussed above, nested PCR involves target amplification performed in two stages. In the first-stage, targets are amplified, illustratively from genomic or reverse-transcribed template. The first-stage amplification may be terminated prior to plateau phase, if desired. In the secondary reaction, the first-stage amplicons may be diluted and a secondary amplification uses the same primers or illustratively uses nested primers hybridizing internally to the primers of the first-stage product. Advantages of nested PCR include: a) the initial reaction product forms a homogeneous and specific template assuring high fidelity in the secondary reaction, wherein even a relatively low-efficiency first-stage reaction creates adequate template to support robust second-stage reaction; b) nonspecific products from the first-stage reaction do not significantly interfere with the second stage reaction, as different nested primers are used and the original amplification template (illustratively genomic DNA or reverse-transcription product) may be diluted to a degree that eliminates its significance in the secondary amplification; and c) nested PCR enables higher-order reaction multiplexing. First-stage reactions can include primers for several unique amplification products. These products are then identified in the second-stage reactions. However, it is understood that first-stage multiplex and second-stage singleplex is illustrative only and that other configurations are possible. For example, the first-stage may amplify a variety of different related amplicons using a single pair of primers, and second-stage may be used to target differences between the amplicons, illustratively using melting curve analysis.

Figure 4:
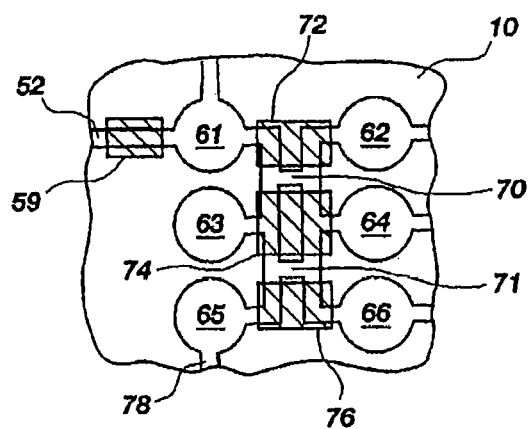
FIG. 4 shows an embodiment of the first-stage amplification zone of the flexible pouch according to FIG. 1.

Turning back to FIG. 1, the nucleic acid sample enters the first-stage amplification zone 60 via channel 52 and is delivered to blister 61. A PCR mixture, including a polymerase (illustratively a Taq polymerase), dNTPs, and primers, illustratively a plurality of pairs of primers for multiplex amplification, may be provided in blister 61 or may be introduced into blister 61 via various means, as discussed above. Alternatively, dried reagents may be spotted onto the location of blister 61 upon assembly of pouch 10, and water or buffer may be introduced to blister 61, illustratively via plunger 68, as shown in FIG. 1. As best seen in FIG. 4, the sample is now secured in blister 61 by pinch valves 59 and 72, and is thermocycled between two or more temperatures, illustratively by heat blocks or Peltier devices that are located in the instrument and configured to contact blister 61. However, it is understood that other means of heating and cooling the sample contained within blister 61, as are known in the art, are within the scope of this invention. Non-limiting examples of alternative heating/cooling devices for thermal cycling include having a air-cycled blister within the bladder, in which the air in the pneumatic blister adjacent blister 61 is cycled between two or more temperatures; or moving the sample to temperature zones within the blister 61, illustratively using a plurality of pneumatic presses, as in U.S. patent application Ser. No. 10/478,453, herein incorporated by reference, or by translating pouch 10 on an axis or providing pouch 10 with a rotary layout and spinning pouch 10 to move the contents between heat zones of fixed temperature.

Nucleic acids from pathogens are often co-isolated with considerable quantities of host nucleic acids. These host-derived nucleic acids often interact with primers, resulting in amplification of undesired products that then scavenge primers, dNTPs, and polymerase activity, potentially starving a desired product of resources. Nucleic acids from pathogenic organisms are generally of low abundance, and undesired product is a potential problem. The number of cycles in the first-stage reaction of zone 60 may be optimized to maximize specific products and minimize non-specific products. It is expected that the optimum number of cycles will be between about 10 to about 30 cycles, illustratively between about 15 to about 20 cycles, but it is understood that the number of cycles may vary depending on the particular target, host, and primer sequence.

Following the first-stage multiplex amplification, the first-stage amplification product is diluted, illustratively in incomplete PCR master mix, before fluidic transfer to secondary reaction sites.

FIG. 4 shows an illustrative embodiment for diluting the sample in three steps. In the first step, pinch valve 72 is opened and the sample undergoes a two-fold dilution by mixing the sample in blister 61 with an equal volume of water or buffer from blister 62, which is provided to blister 62, as well as blisters 64 and 66, as discussed above. Squeezing the volume back and forth between blisters 61, 62 provides thorough mixing. As above, mixing may be provided by pneumatic bladders provided in the bladder 710 and located adjacent blisters 61, 62. The pneumatic bladders may be alternately pressurized, forcing the liquid back and forth. During mixing, a pinch valve 74 prevents the flow of liquid into the adjacent blisters. At the conclusion of mixing, a volume of the diluted sample is captured in region 70, and pinch valve 72 is closed, sealing the diluted sample in region 70. Pinch valve 74 is opened and the sample is further diluted by water or buffer provided in either or both of blisters 63, 64. As above, squeezing the volume back and forth between blisters 63, 64 provides mixing. Subsequently, pinch valve 74 is closed, sealing a further diluted volume of sample in region 71. Final dilution takes place illustratively by using buffer or water provided in either or both of blisters 65, 66, with mixing as above. Illustratively this final dilution takes place using an incomplete PCR master mix (e.g., containing all PCR reagents except primers) as the fluid. Optional heating of the contents of blister 66 prior to second-stage amplification can provide the benefits of hot-start amplification without the need for expensive antibodies or enzymes. It is understood, however, that water or other buffer may be used for the final dilution, with additional PCR components provided in second-stage amplification zone 80. While the illustrative embodiment uses three dilution stages, it is understood that any number of dilution stages may be used, to provide a suitable level of dilution. It is also understood that the amount of dilution can be controlled by adjusting the volume of the sample captured in regions 70 and 71, wherein the smaller the amount of sample captured in regions 70 and 71, the greater the amount of dilution or wherein additional aliquots captured in region 70 and/or region 71 by repeatedly opening and closing pinch valves 72 and 74 and/or pinch valves 74 and 76 may be used to decrease the amount of dilution. It is expected that about $10^{-2}$ to about $10^{-5}$ dilution would be suitable for many applications.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 10 may require accommodations be made to compensate for a less pure preparation. PCR may be inhibited by components of biological samples, which is a potential obstacle. Illustratively, hot-start PCR, higher concentration of taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

While dilution and second-stage sample preparation are accomplished in the illustrative embodiment by retaining a small amount of amplified sample in the blisters and channels of the first-stage PCR portion of the pouch, it is understood that these processes may also be performed in other ways. In one such illustrative example, pre-amplified sample can be captured in a small cavity in a member, illustratively a translating or rotating member, able to move a fixed volume of sample from the first to the second-stage PCR reagent. A one microliter fraction of the pre-amplified sample, mixed with 100 microliters of fresh PCR reagent would yield a one-hundred-fold reduction in concentration. It is understood that this dilution is illustrative only, and that other volumes and dilution levels are possible. This approach could be accomplished by forcing the first-stage amplification product into the rigid fitment where it contacts one of the plungers 68 or 69 of FIG. 1. In such an embodiment, the plunger would be configured to carry a small fraction of the sample into contact with the adjacent dilution buffer or second-stage PCR buffer. Similarly a sliding element could be used to carry a small amount of the first-stage amplification product into contact with the second-stage reaction mix while maintaining a seal between the stages, and containing the amplified sample within the rigid fitment 90.

Subsequent to first-stage PCR and dilution, channel 78 transfers the sample to a plurality of low volume blisters 82 for secondary nested PCR. In one illustrative embodiment, dried primers provided in the second-stage blisters are resuspended by the incoming aqueous material to complete the reaction mixture. Optionally, fluorescent dyes such as LCGreen® Plus (Idaho Technology, Salt Lake City, UT) used for detection of double-stranded nucleic acid may be provided in each blister or may be added to the incomplete PCR master mix provided at the end of the serial dilution, although it is understood that LCGreen® Plus is illustrative only and that other dyes are available, as are known in the art. In another optional embodiment, dried fluorescently labeled oligonucleotide probes configured for each specific amplicon may be provided in each respective second-stage blister, along with the respective dried primers. Further, while pouch 10 is designed to contain all reactions and manipulations within, to reduce contamination, in some circumstances it may be desirable to remove the amplification products from each blister 82 to do further analysis. Other means for detection of the second-stage amplicon, as are known in the art, are within the scope of this invention. Once the sample is transferred to blisters 82, pinch valves 84 and 86 are activated to close off blisters 82. Each blister 82 now contains all reagents needed for amplification of a particular target. Illustratively, each blister may contain a unique pair of primers, or a plurality of blisters 82 may contain the same primers to provide a number of replicate amplifications.

It is noted that the embodiments disclosed herein use blisters for the second-stage amplification, wherein the blisters are formed of the same or similar plastic film as the rest of the flexible portion. However, in many embodiments, the contents of the second-stage blisters are never removed from the second-stage blisters, and, therefore, there is no need for the second-stage reaction to take place in flexible blisters. It is understood that the second-stage reaction may take place in a plurality of rigid, semi-rigid, or flexible chambers that are fluidly connected to the blisters. The chambers could be sealed as in the present example by placing pressure on flexible channels that connect the chambers, or may be sealed in other ways, illustratively by heat sealing or use of one-way valves. Various embodiments discussed herein include blisters provided solely for the collection of waste. Since the waste may never be removed, waste could be collected in rigid, semi-rigid, or flexible chambers.

It is within the scope of this invention to do the second-stage amplification with the same primers used in the first-stage amplification (see U.S. Pat. No. 6,605,451). However, it is often advantageous to have primers in second-stage reactions that are internal to the first-stage product such that there is no or minimal overlap between the first- and second-stage primer binding sites. Dilution of first-stage product largely eliminates contribution of the original template DNA and first-stage reagents to the second-stage reaction. Furthermore, illustratively, second-stage primers with a Tm higher than those used in the first-stage may be used to potentiate nested amplification. Primer may be designed to avoid significant hairpins, hetero/homo-dimers and undesired hybridization. Because of the nested format, second-stage primers tolerate deleterious interactions far more so than primers used to amplify targets from genomic DNA in a single step. Optionally, hot-start is used on second-stage amplification.

If a fluorescent dye is included in second-stage amplification, illustratively as a dsDNA binding dye or as part of a fluorescent probe, as are known in the art, optics provided may be used to monitor amplification of one or more of the samples. Optionally, analysis of the shape of the amplification curve may be provided to call each sample positive or negative. Illustrative methods of calling the sample are discussed in U.S. Pat. No. 6,730,501, herein incorporated by reference. Alternatively, methods employing a crossing threshold may be used. A computer may be provided externally or within the instrument and may be configured to perform the methods and call the sample positive or negative based upon the presence or absence of second-stage amplification and may provide quantitative information about the starting template concentration by comparing characteristic parameters of the amplification curve (such as crossing threshold) to standard curves, or relative to other amplification curves within the run. It is understood, however, that other methods, as are known in the art, may be used to call each sample. Other analyses may be performed on the fluorescent information. One such non-limiting example is the use of melting curve analysis to show proper melting characteristics (e.g. Tm, melt profile shape) of the amplicon. The optics provided may be configured to capture images of all blisters 82 at once, or individual optics may be provided for each individual blister. Other configurations are within the scope of this invention.

Figures 5, 5A, 5B:
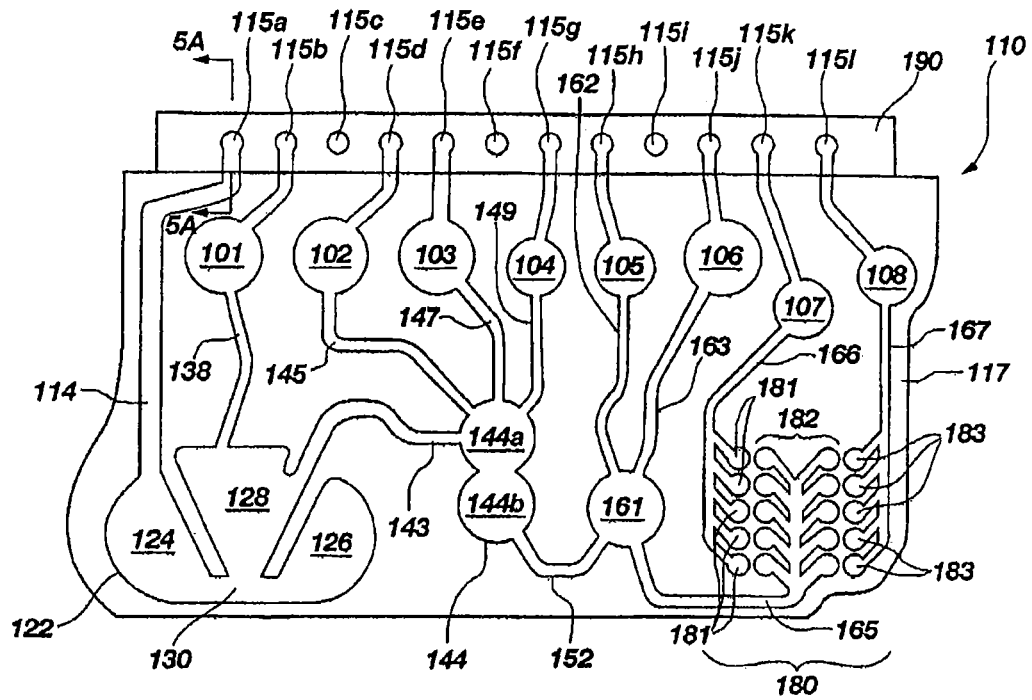
FIG. 5 is similar to FIG. 1, except showing an alternative embodiment of a pouch.
FIG. 5a is a cross-sectional view of the fitment of the pouch of FIG. 5.
FIG. 5b is an enlargement of a portion of the pouch of FIG. 5.

FIG. 5 shows an alternative pouch 110. In this embodiment, various reagents are loaded into pouch 110 via fitment 190. FIG. 5a shows a cross-section of fitment 190 with one of a plurality of plungers 168. It is understood that, while FIG. 5a shows a cross-section through entry channel 115a, as shown in the embodiment of FIG. 5, there are 12 entry channels present (entry channel 115a through 115l), each of which may have its own plunger 168 for use in fitment 190, although in this particular configuration, entry channels 115c, 115f, and 115i are not used. It is understood that a configuration having 12 entry channels is illustrative only, and that any number of entry channels and associated plungers may be used. In the illustrative embodiment, an optional vacuum port 142 of fitment 190 is formed through a first surface 194 of fitment 190 to communicate with chamber 192. Optional vacuum port 142 may be provided for communication with a vacuum or vacuum chamber (not shown) to draw out the air from within pouch 110 to create a vacuum within chamber 192 and the various blisters and chambers of pouch 110. Plunger 168 is then inserted far enough into chamber 192 to seal off vacuum port 142. Chamber 192 is illustratively provided under a predetermined amount of vacuum to draw a desired volume of liquid into chamber 192 upon use. Additional information on preparing chamber 192 may be found in U.S. patent application Ser. No. 10/512,255, already incorporated by reference.

Illustrative fitment 190 further includes an injection port 141 formed in the second surface 195 of fitment 190. Illustratively, injection port 141 is positioned closer to the plastic film portion of pouch 110 than vacuum port 142, as shown in FIG. 5a, such that the plunger 168 is inserted far enough to seal off vacuum port 142, while still allowing access to chamber 192 via injection port 141. As shown, second surface 119 of plastic film portion 117 provides a penetrable seal 139 to prevent communication between chamber 192 and the surrounding atmosphere via injection port 141. However, it is understood that second surface 119 optionally may not extend to injection port 141 and various other seals may be employed. Further, if another location for the seal is desired, for example on a first surface 194 of fitment 190, injection port 141 may include a channel to that location on fitment 190. U.S. patent application Ser. No. 10/512,255, already incorporated by reference, shows various configurations where the seal is located remotely from the injection port, and the seal is connected to the chamber via a channel. Also, U.S. patent application Ser. No. 10/512,255 discloses various configurations where channels connect a single seal to multiple chambers. Variations in seal location, as well as connection of a single injection port to multiple chambers, are within the scope of this invention. Optionally, seal 139 may be frangible and may be broken upon insertion of a cannula (not shown), to allow a fluid sample from within the cannula to be drawn into or forced into chamber 192.

The illustrative plunger 168 of the pouch assembly 110 is cylindrical in shape and has a diameter of approximately 5 mm to be press-fit into chamber 192. Plunger 168 includes a first end portion 173 and an opposite second end portion 175. As shown in FIG. 5a, a notch 169 of plunger 168 is formed in second end portion 175. In use, second end portion 175 is inserted part way into chamber 192, and notch 169 may be aligned with injection port 141 to allow a fluid sample to be drawn into or injected into chamber 192, even when plunger 168 is inserted far enough that plunger 168 would otherwise be blocking injection port 141.

Illustratively, a fluid is placed in a container (not shown) with a syringe having a cannulated tip that can be inserted into injection port 141 to puncture seal 139 therein. In using an air-evacuated pouch assembly 110, when seal 139 is punctured, the fluid is withdrawn from the container due to the negative pressure within chamber 192 relative to ambient air pressure. Fluid then passes through port 141 to fill chamber 192. At this point, the fluid usually does not flow into the plastic film portion 117 of pouch 110. Finally, the plunger 168 is inserted into chamber 192 such that second end portion 175 of plunger 168 approaches the bottom 191 of chamber 192, to push a measured amount of the reagent or sample into the plastic film portion 117. As shown, plunger 168 is configured such that upon full insertion, second end portion 175 does not quite meet bottom 191 of chamber 192. The remaining space is useful in trapping bubbles, thereby reducing the number of bubbles entering plastic film portion 117. However, in some embodiments it may be desirable for second end portion 175 to meet bottom 191 upon full insertion of plunger 168. In the embodiment shown in FIG. 5, entry channels 115a, 115b, 115d, 115e, 115g, 115h, 115j, 115k, and 115l all lead to reaction zones or reservoir blisters. It is understood that full insertion of the plunger associated with entry channel 115a would force a sample into three-lobed blister 122, full insertion of the plunger associated with entry channel 115b would force a reagent into reservoir blister 101, full insertion of the plunger associated with entry channel 115d would force a reagent into reservoir blister 102, full insertion of the plunger associated with entry channel 115e would force a reagent into reservoir blister 103, full insertion of the plunger associated with entry channel 115g would force a reagent into reservoir blister 104, full insertion of the plunger associated with entry channel 115h would force a reagent into reservoir blister 105, full insertion of the plunger associated with entry channel 115j would force a reagent into reservoir blister 106, full insertion of the plunger associated with entry channel 115k would force a reagent into reservoir blister 107, and full insertion of the plunger associated with entry channel 115l would force a reagent into reservoir blister 108.

If a plunger design is used including notch 169 as illustrated in the embodiment shown in FIG. 5a, the plunger 168 may be rotated prior to being lowered, so as to offset notch 169 and to close off injection port 141 from communication with chamber 192, to seal the contents therein. This acts to minimize any potential backflow of fluid through injection port 141 to the surrounding atmosphere, which is particularly useful when it is desired to delay in full insertion of the plunger. Although notch 169 is shown and described above with respect to plunger 168, it is within the scope of this disclosure to close off injection port 141 soon after dispensing the fluid sample into the chamber 192 by other means, such as depressing plunger 168 toward the bottom of chamber 192, heat sealing, unidirectional valves, or self-sealing ports, for example. If heat sealing is used as the sealing method, a seal bar could be included in the instrument such that all chambers are heat sealed upon insertion of the pouch into the instrument.

Figure 6:
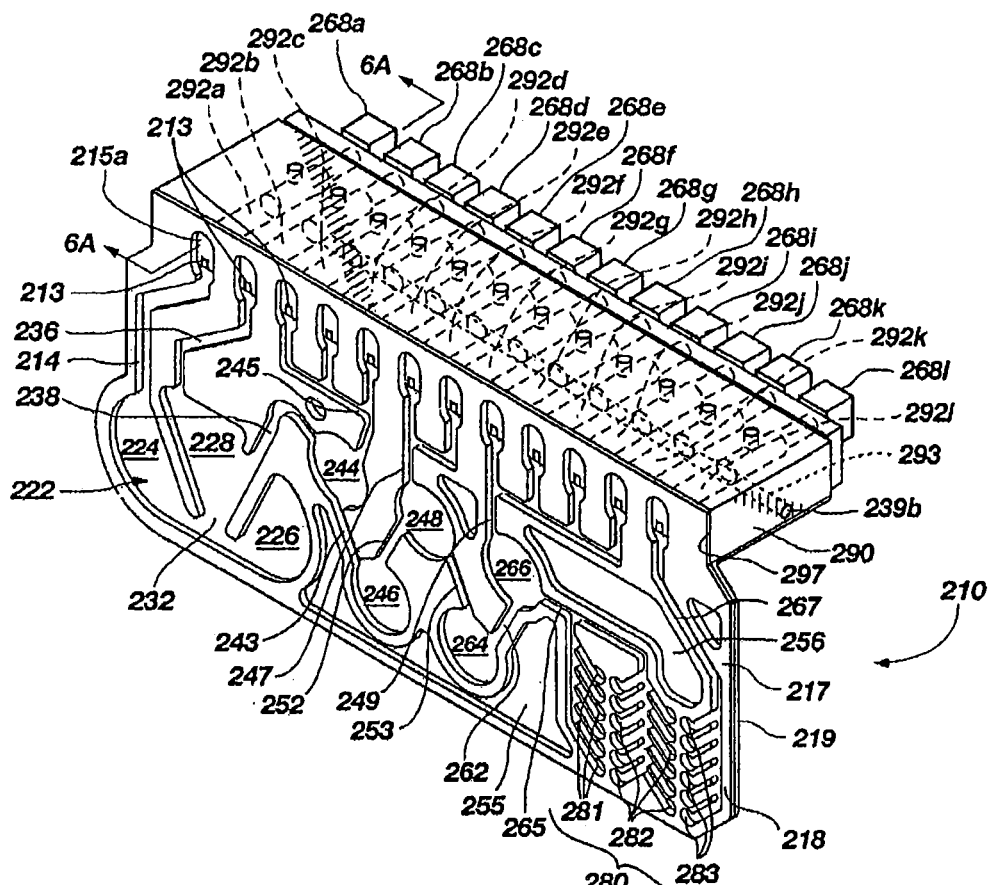
FIG. 6 is a perspective view of another alternative embodiment of a pouch.
Figure 6A:
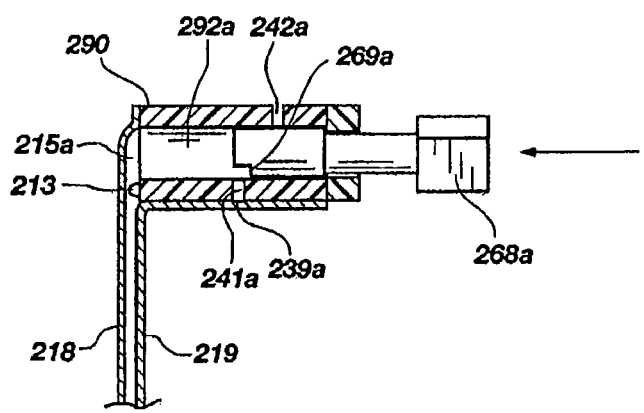
FIG. 6a is a cross-sectional view of the fitment of the pouch of FIG. 6.

In the illustrative method, the user injects the sample into the injection port 141 associated with entry channel 115a, and water into the various other injection ports. The water rehydrates reagents that have been previously freeze-dried into chambers 192 associated with each of entry channels 115b, 115d, 115e, 115g, 115h, 115j, 115k, and 115l. The water may be injected through one single seal and then be distributed via a channel to each of the chambers, as shown in FIG. 6 below, or the water could be injected into each chamber independently. Alternatively, rather than injecting water to rehydrate dried reagents, wet reagents such as lysis reagents, nucleic acid extraction reagents, and PCR reagents may be injected into the appropriate chambers 192 of the fitment 190.

Figure 8:
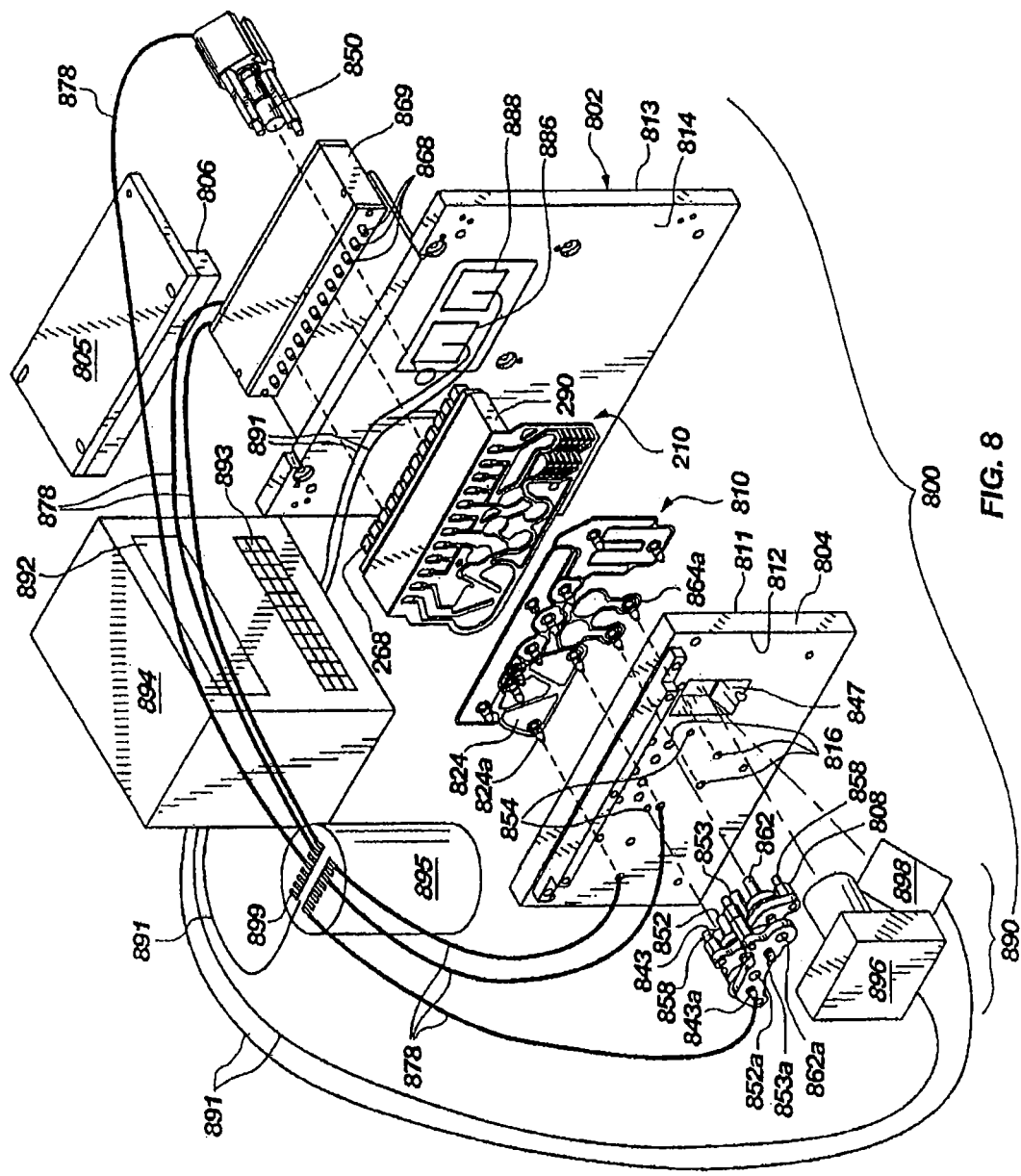
FIG. 8 is an exploded perspective view of an instrument for use with the pouch of FIG. 6, including the pouch of FIG. 6.

Upon activation of the plunger 168 associated with entry channel 115a, the sample is forced directly into three-lobed blister 122 via channel 114. The user also presses the remaining plungers 168, forcing the contents out of each of the chambers 192 in fitment 190 and into reservoir blisters 101 through 108. At this point, pouch 110 is loaded into an instrument for processing. While instrument 800, shown in FIG. 8, is configured for the pouch 210 of FIG. 6, it is understood that modification of the configuration of the bladders of instrument 800 would render instrument 800 suitable for use with pouches 110 and 510, or with pouches of other configurations.

In one illustrative example, upon depression of the plungers 168, reservoir blister 101 now contains DNA-binding magnetic beads in isopropanol, reservoir blister 102 now contains a first wash solution, reservoir blister 103 now contains a second wash solution, reservoir blister 104 now contains a nucleic acid elution buffer, reservoir blister 105 now contains first-stage PCR reagents, including multiplexed first-stage primers, reservoir blister 106 now contains second-stage PCR reagents without primers, reservoir blister 107 now contains negative control PCR reagents without primers and without template, and reservoir blister 108 now contains positive control PCR reagents with template. However, it is understood that these reagents are illustrative only, and that other reagents may be used, depending upon the desired reactions and optimization conditions.

Once pouch 110 has been placed into instrument 800 and the sample has been moved to three-lobed blister 122, the sample may be subjected to disruption by agitating the sample with lysing particles such as ZS or ceramic beads.

The lysing particles may be provided in three-lobed blister 122, or may be injected into three-lobed blister 122 along with the sample. The three-lobed blister 122 of FIG. 5 is operated in much the same way as three-lobed blister 22 of FIG. 1, with the two lower lobes 124, 126 pressurized together, and pressure is alternated between the upper lobe 128 and the two lower lobes 124, 126. However, as illustrated, lower lobes 124, 126 are much more rounded than lower lobes 24, 26, allowing for a smooth flow of beads to channel 130 and allowing for high-speed collisions, even without the triangular flow separator at nexus 32. As with three-lobed blister 22, three-lobed blister 122 of FIG. 5 allows for effective lysis or disruption of microorganisms, cells, and viral particles in the sample. It has been found that a channel 130 having a width of about 3-4 mm, and illustratively about 3.5 mm, remains relatively clear of beads during lysis and is effective in providing for high-velocity collisions.

After lysis, nucleic-acid-binding magnetic beads are injected into upper lobe 128 via channel 138 by pressurizing a bladder positioned over reservoir blister 101. The magnetic beads are mixed, illustratively more gently than with during lysis, with the contents of three-lobed blister 122, and the solution is incubated, illustratively for about 1 minute, to allow nucleic acids to bind to the beads.

The solution is then pumped into the "FIG. 8" blister 144 via channel 143, where the beads are captured by a retractable magnet housed in the instrument, which is illustratively pneumatically driven. The bead capture process begins by pressurizing all lobes 124, 126, and 128 of the bead milling apparatus 122. This forces much of the liquid contents of 122 through channel 143 and into blister 144. A magnet is brought into contact with the lower portion 144b of blister 144 and the sample is incubated for several seconds to allow the magnet to capture the beads from the solution, then the bladders adjacent to blister 122 are depressurized, the bladders adjacent blister portions 144a and 144b are pressurized, and the liquid is forced back into blister 122. Since not all of the beads are captured in a single pass, this process may be repeated up to 10 times to capture substantially all of the beads in blister 144. Then the liquid is forced out of blister 144, leaving behind only the magnetic beads and the captured nucleic acids, and wash reagents are introduced into blister 144 in two successive washes (from reservoir blisters 102 and 103 via channels 145 and 147, respectively). In each wash, the bladder positioned over the reservoir blister containing the wash reagent is pressurized, forcing the contents into blister 144. The magnet is withdrawn and the pellet containing the magnetic beads is disrupted by alternatively pressurizing each of two bladders covering each lobe 144a and 144b of blister 144. When the upper lobe 144a is compressed, the liquid contents are forced into the lower lobe 144b, and when the lower lobe 144b is compressed, the contents are forced into the upper lobe 144a. By agitating the solution in blister 144 between upper lobe 144a and lower lobe 144b, the magnetic beads are effectively washed of impurities. A balance is maintained between inadequate agitation, leaving the pellet of beads undisturbed, and excessive agitation, potentially washing the nucleic acids from the surface of the beads and losing them with the wash reagents. After each wash cycle, the magnetic beads are captured via the magnet in blister 144 and the wash reagents are illustratively forced into three-lobed blister 122, which now serves as a waste receptacle. However, it is understood that the used reservoir blisters may also serve as waste receptacles, or other blisters may be provided specifically as waste receptacles.

Nucleic acid elution buffer from reservoir blister 104 is then injected via channel 149 into blister 144, the sample is once again agitated, and the magnetic beads are recaptured by employment of the magnet. The fluid mixture in blister 144 now contains nucleic acids from the original sample. Pressure on blister 144 moves the nucleic acid sample to the first stage PCR blister 161 via channel 152, where the sample is mixed with first-stage PCR master mix containing multiple primer sets, the PCR master mix provided from reservoir blister 105 via channel 162. If desired, the sample and/or the first-stage PCR master mix may be heated prior to mixing, to provide advantages of hot star. Optionally, components for reverse transcription of RNA targets may be provided prior to first-stage PCR. Alternatively, an RT enzyme, illustratively a thermostable RT enzyme may be provided in the first-stage PCR master mix to allow for contemporaneous reverse transcription of RNA targets. It is understood that an RT enzyme may be present in the first-stage PCR mixture in any of the embodiments disclosed herein. As will be seen below, pouch 110 of FIG. 5 is configured for up to 10 primer sets, but it is understood that the configuration may be altered and any number of primer sets may be used. A bladder positioned over blister 161 is pressurized at low pressure, to force the contents of blister 161 into intimate contact with a heating/cooling element, illustratively a Peltier element, on the other side of blister 161. The pressure on blister 161 should be sufficient to assure good contact with the heating/cooling element, but should be gentle enough such that fluid is not forced from blister 161. The heating/cooling element is temperature cycled, illustratively between about 60° C. to about 95° C. Illustratively, temperature cycling is performed for about 15-20 cycles, resulting in amplification of one or more nucleic acid targets present. Also illustratively, temperature cycling ceases prior to plateau phase, and may cease in log phase or even prior to log phase. In one example, it may be desirable merely to enrich the sample with the desired amplicons, without reaching minimal levels of detection. See U.S. Pat. No. 6,605,451, herein incorporated by reference.

The amplified sample is optionally then diluted by forcing most the sample back into blister 144 via channel 152, leaving only a small amount (illustratively about 1 to 5%) of the amplified sample in blister 161, and second-stage PCR master mix is provided from reservoir blister 106 via channel 163. The sample is thoroughly mixed illustratively by moving it back and forth between blisters 106 and 161 via channel 163. If desired, the reaction mixture may be heated to above extension temperature, illustratively at least 60° C., prior to second-stage amplification. The sample is then forced through channel 165 into an array of low volume blisters 182 in the center of second-stage amplification zone 180. Each of the ten illustrative low volume blisters 182 may contain a different primer pair, either essentially the same as one of the primer pairs in the first-stage amplification, or "nested" within the first-stage primer pair to amplify a shortened amplicon. The primers, now hydrated by the sample, complete the amplification mixture. Positive and negative control samples are also introduced by pressurizing the contents of reservoir blisters 107 and 108, respectively, forcing PCR master mix either without target DNA from reservoir blister 107 via channel 166, or with control DNA from reservoir blister 108, via channel 167. As illustrated, there are five each of positive control blisters 183 and negative control blisters 181, which may be multiplexed 2-fold to provide the necessary controls for ten different second-stage amplification reactions. It is understood that this configuration is illustrative only and that any number of second-stage blisters may be provided.

Illustratively, the PCR master mix used for second-stage amplification lacks the primers, but is otherwise complete. However, an "incomplete" PCR master mix may lack other PCR components as well. In one example, the second-stage PCR master mix is water or buffer only, which is then mixed with the optionally diluted first-stage PCR amplification product. This mixture is moved to the small-volume PCR reaction blisters, where all of the remaining components have been previously provided. If desired, all of the remaining components may be mixed together and spotted as a single mixture into the small-volume PCR reaction blisters. Alternatively, as illustrated in FIG. 5b, each of the components may be spotted onto a separate region of the small-volume PCR reaction blister 182. As shown in FIG. 5b, four regions are present, illustratively with dNTPs spotted at region 182a, primers spotted at 182b, polymerase spotted at 182c, and a magnesium compound spotted at 182d. By spotting the components separately and heating the sample mixture prior to rehydrating the components, nonspecific reactions can be minimized. It is understood that any combination of components can be spotted this way, and that this method of spotting components into one or more regions of the blisters may be used with any embodiment of the present invention.

The channels 165, 166, and 167 leading to the small-volume PCR reaction blisters 181, 182, and 183 are sealed, and a pneumatic bladder gently presses the array against a heating/cooling element, illustratively a Peltier element, for thermal cycling. The cycling parameters may be independently set for second-stage thermal cycling. Illustratively, the reactions are monitored by focusing an excitation source, illustratively a blue light (450-490 nm), onto the array, and imaging the resultant fluorescent emissions, illustratively fluorescent emissions above 510 nm.

In the above example, pinch valves are not discussed. However, it is understood that when it is desired to contain a sample in one of the blisters, pneumatic actuators positioned over channels leading to and from the particular blister are pressurized, creating pinch valves and closing off the channels. Conversely, when it is desired to move a sample from one of the blisters, the appropriate pneumatic actuator is depressurized, allowing the sample flow through the channel.

The pouch described above in FIG. 5 includes reagent reservoir blisters 101 through 108, in which the user injected reagents from the fitment 190 into the reagent reservoir blisters 101 through 108 in the plastic film portion 117 of the pouch 110, illustratively prior to insertion of pouch 110 into the instrument. While there are advantages to the use of the reagent reservoir blisters of FIG. 5, including having the ability to maintain the contents of the various blisters at different temperatures, there are some disadvantages as well. Because the operator is responsible for moving the reagents from the fitment 190 to the reservoir blisters 101 through 108, and because this is often done outside of the machine and thus without activated pinch valves, reagents could occasionally leak from the reservoir blisters to the working blisters. The reagents in reservoir blisters are exposed during preparation and loading. If they are pressed, squeezed, or even lightly bumped, the reagents may leak through available channels. If the loss of reagents is substantial, the reaction may fail completely. Furthermore, during operation there may be some variability in the amount of reagent forced from the reservoir blisters 101 through 108, leading to inconsistent results. Automation of introduction of the reagents to fitment 190 and movement of the reagents from fitment 190 to reagent reservoir blisters 101 through 108 would solve many of these problems, and is within the scope of this invention.

The pouch 210 of FIG. 6 addresses many of these issues in a different way, by using a direct-injection approach wherein the instrument itself moves the plungers 268, illustratively via pneumatic pistons, and forces the reagents into the various working blisters as the reagents are needed. Rather than storing the reagents in reservoir blisters 101 through 108 of FIG. 5, in the embodiment of FIG. 6 the reagents are introduced into various chambers 292 of fitment 290 and are maintained there until needed. Pneumatic operation of piston 268 at the appropriate time introduces a measured amount of the reagent to the appropriate reaction blister. In addition to addressing many of the above-mentioned issues, pouch 210 also has a much more compact shape, allowing for a smaller instrument design, and pouch 210 has shorter channels, permitting better fluid flow and minimizing reagent loss in channels.

In one illustrative embodiment of FIG. 6, a 300 µl mixture comprising the sample to be tested (100 µl) and lysis buffer (200 µl) is injected into injection port 241a. Water is also injected into the fitment 290 via seal 239b, hydrating up to eleven different reagents, each of which were previously provided in dry form in chambers 292b through 292l via channel 293 (shown in shadow). These reagents illustratively may include freeze-dried PCR reagents, DNA extraction reagents, wash solutions, immunoassay reagents, or other chemical entities. For the example of FIG. 6, the reagents are for nucleic acid extraction, first-stage multiplex PCR, dilution of the multiplex reaction, and preparation of second-stage PCR reagents, and control reactions. In the embodiment shown in FIG. 6, all that need be injected is the sample in port 241a and water in port 241b.

As shown in FIG. 6, water injected via seal 293b is distributed to various chambers via channel 293. In this embodiment, only the sample and water need be injected into pouch 210. It is understood, however, that water could be injected into each chamber 292 independently. Further, it is understood that, rather than providing dried reagents in the various chambers 292 and hydrating upon injection of the water, specific wet reagents could be injected into each chamber, as desired. Additionally, it is understood that one or more of chambers 292 could be provided with water only, and the necessary reagents may be provided dried in the appropriate reaction blisters. Various combinations of the above, as dictated by the needs of the particular reaction, are within the scope of this invention.

As seen in FIG. 6, optional protrusions 213 are provided on bottom surface 297 of fitment 290. As shown, protrusions 213 are located within their respective entry channels 215. However, other configurations are possible. Protrusions 213 assist in opening entry channel 215 and prevent bottom surface 297 from engaging another flat surface in such a way to pinch off entry channels 215 when plungers 268 are depressed, which helps prevent back-flow upon activation of the plungers 268. Such protrusions may be used on any of the various pouches according to the present invention.

In embodiments wherein water is injected into the pouch to hydrate multiple dry reagents in multiple chambers in the fitment, a means of closing the channel between the injection port and the many chambers is desired. If the channel is not closed, activation of each plunger may force some of the contents of its respective chamber back out into the channel, potentially contaminating neighboring chambers and altering the volumes contained in and delivered from the chamber. Several ways of closing this channel have been used, including rotating a notched plunger 268 as discussed above, and heat-sealing the plastic film across the channel thereby closing the channel permanently, and applying pressure to the channel as a pinch valve. Other closures may also be used, such as valves built into the fitment, illustratively one-way valves.

Figure 7:
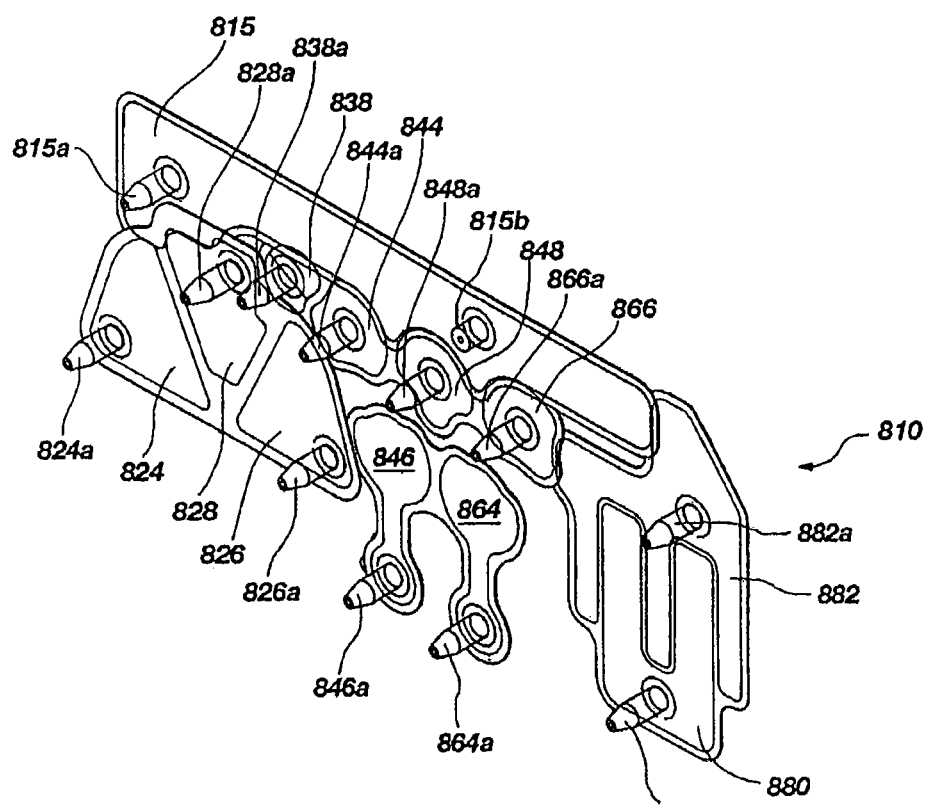
FIG. 7 shows illustrative bladder components for use with the pouch of FIG. 6.

After the fluids are loaded into chambers 292 and pouch 210 is loaded into the instrument, plunger 268a is depressed illustratively via activation of a pneumatic piston, forcing the balance of the sample into three-lobed blister 220 via channel 214. As with the embodiments shown in FIGS. 1 and 5, the lobes 224, 226, and 228 of three-lobed blister 220 are sequentially compressed via action bladders 824, 826, and 828 of bladder assembly 810, shown in FIGS. 7-9, forcing the liquid through the narrow nexus 232 between the lobes, and driving high velocity collisions, shearing the sample and liberating nucleic acids, illustratively including nucleic acids from hard-to-open spores, bacteria, and fungi. Cell lysis continues for an appropriate length of time, illustratively 0.5 to 10 minutes.

Once the cells have been adequately lysed, plunger 268b is activated and nucleic acid binding magnetic beads stored in chamber 292b are injected via channel 236 into upper lobe 228 of three-lobed blister 220. The sample is mixed with the magnetic beads and the mixture is allowed to incubate for an appropriate length of time, illustratively approximately 10 seconds to 10 minutes.

The mixture of sample and beads are forced through channel 238 into blister 244 via action of bladder 826, then through channel 243 and into blister 246 via action of bladder 844, where a retractable magnet 850 located in instrument 800 adjacent blister 245, shown in FIG. 8, captures the magnetic beads from the solution, forming a pellet against the interior surface of blister 246. A pneumatic bladder 846, positioned over blister 246 then forces the liquid out of blister 246 and back through blister 244 and into blister 222, which is now used as a waste receptacle. However, as discussed above with respect to FIG. 5, other waste receptacles are within the scope of this invention. One of plungers 268c, 268d, and 268e may be activated to provide a wash solution to blister 244 via channel 245, and then to blister 246 via channel 243. Optionally, the magnet 850 is retracted and the magnetic beads are washed by moving the beads back and forth from blisters 244 and 246 via channel 243, by alternatively pressurizing bladders 844 and 846. Once the magnetic beads are washed, the magnetic beads are recaptured in blister 246 by activation of magnet 850, and the wash solution is then moved to blister 222. This process may be repeated as necessary to wash the lysis buffer and sample debris from the nucleic acid-binding magnetic beads. Illustratively, three washes are done, one each using wash reagents in chambers 292c, 292d, and 292e. However, it is understood that more or fewer washes are within the scope of this invention. If more washes are desired, more chambers 292 may be provided. Alternatively, each chamber 292 may hold a larger volume of fluid and activation of the plungers may force only a fraction of the volume from the chamber upon each activation.

After washing, elution buffer stored in chamber 292f is moved via channel 247 to blister 248, and the magnet is retracted. The solution is cycled between blisters 246 and 248 via channel 252, breaking up the pellet of magnetic beads in blister 246 and allowing the captured nucleic acids to dissociate from the beads and come into solution. The magnet 850 is once again activated, capturing the magnetic beads in blister 246, and the eluted nucleic acid solution is forced into blister 248.

Plunger 268h is depressed and first-stage PCR master mix from chamber 292h is mixed with the nucleic acid sample in blister 248. Optionally, the mixture is mixed by alternative activation of bladders 848 and 864, forcing the mixture between 248 and 264 via channel 253. After several cycles of mixing, the solution is contained in blister 264, where first-stage multiplex PCR is performed. If desired, prior to mixing, the sample may be retained in blister 246 while the first-stage PCR master mix is pre-heated, illustratively by moving the first-stage PCR master mix into blister 264 or by providing a heater adjacent blister 248. As discussed above, this pre-heating may provide the benefits of hot start PCR. The instrument 800 illustrated in FIG. 8 features Peltier-based thermal cyclers 886 and 888 which heat and cool the sample. However, it is understood that other heater/cooler devices may be used, as discussed above. Optionally, mixing between blisters 248 and 264 may continue during temperature cycling, with thermal cycler 886 positioned to heat and cool both blisters 248 and 264. It has been found that such mixing improves the first-stage PCR reaction in some embodiments. Also, thermal cycling can be accomplished by varying the temperatures in two or more different blisters, allowing minimal energy expenditure and maximizing thermal cycling speed. For example the temperature can be maintained at 95° C. in blister 248, and 65° C. blister 264, and moving the sample between these blisters effectively transfers heat into and out of the sample, allowing rapid and accurate thermal cycling. Temperature cycling is illustratively performed for 15-20 cycles, although other levels of amplification may be desirable, depending on the application, as discussed above. As will be seen below, the second-stage amplification zone 280 is configured to detect amplification in 18 second-stage reactions. Accordingly, 18 different primer-pairs may be included in the PCR reaction in blister 264.

In an alternative hot start method, pouch 210 is manufactured with the primers provided in one of the blisters, illustratively blister 264. In one embodiment, the primers are freeze dried separately and then introduced during manufacture into blister 264 as a friable pellet. Prior to first-stage PCR, illustratively the sample is eluted from blister 246 and pushed to blister 264 to rehydrate the primer pellet. Peltier 886, which is positioned adjacent blisters 248 and 264 is heated to 48° C., and PCR master mix is pushed to blister 248. After a hold, illustratively for 10 seconds, during which the two blisters reach 48° C., mixing between blisters 248 and 264 begins. Thus, the enzymes and dNTPs remain in blister 248 and most of the sample and the primers remain in blister 264 until the components separately have reached 48° C. It is understood, however, that the choice of 48° C. was made for use with concurrent first-stage amplification and RT using AMV, which is active up to 50° C. If RT is not needed or a more thermostable RT enzyme is used, then one or both of the two blisters 248 and 264 may be heated up to 58° C., or even higher, depending on the primer melting temperature or other factors in a particular first-stage amplification protocol. It is understood that this hot start method may be used with any embodiment of the present invention.

In an alternative embodiment, to reduce the complexity of the first-stage PCR reaction, blister 248 may be divided into two or more blisters. It is believed that the number of nonspecific products of a multiplex reaction goes up as the square (or possibly higher power) of the number of primers in the mixture, while the loss of sensitivity of an assay is a linear function of the amount of input sample. Thus, for example, splitting the first stage PCR into two reactions, each of half the volume of the single reaction of this embodiment, would reduce sensitivity by two-fold but the quantity and complexity of the nonspecific reactions would be ¼ as much. If blister 248 is divided into or more blisters, blister 264 may be divided into a number of blisters equal to the number of blisters 248. Each respective blister 248 would be connected to its respective blister 264 via a respective channel 253. Each blister 264 would be provided with a pellet comprising a subset of all primers. Sample from blister 246 would be divided across each blister 248, each blister 248 would be sealed from all others, and thermal cycling would proceed with each pair of blisters 248 and 264, as described above. After thermal cycling, the sample would be recombined into blister 266 or individually sent to separate sets of second-stage blisters.

After first-stage PCR has proceeded for the desired number of cycles, the sample may be diluted as discussed above with respect to the embodiment of FIG. 5, by forcing most of the sample back into blister 248, leaving only a small amount, and adding second-stage PCR master mix from chamber 292i. Alternatively, a dilution buffer from 292i may be moved to blister 266 via channel 249 and then mixed with the amplified sample in blister 264 by moving the fluids back and forth between blisters 264 and 266. After mixing, a portion of the diluted sample remaining in blister 264 is forced away to three-lobed blister 222, now the waste receptacle. If desired, dilution may be repeated several times, using dilution buffer from chambers 292j and 292k, and then adding second-stage PCR master mix from chamber 292g to some or all of the diluted amplified sample. It is understood that the level of dilution may be adjusted by altering the number of dilution steps or by altering the percentage of the sample discarded prior to mixing with the dilution buffer or second-stage PCR master mix. If desired, this mixture of the sample and second-stage PCR master mix may be pre-heated in blister 264 prior to movement to second-stage blisters 282 for second-stage amplification. As discussed above, such preheating may obviate the need for a hot-start component (antibody, chemical, or otherwise) in the second-stage PCR mixture.

The illustrative second-stage PCR master mix is incomplete, lacking primer pairs, and each of the 18 second-stage blisters 282 is pre-loaded with a specific PCR primer pair. If desired, second-stage PCR master mix may lack other reaction components, and these components may then be pre-loaded in the second-stage blisters 282 as well. As discussed above with the prior examples, each primer pair may be identical to a first-stage PCR primer pair or may be nested within the first-stage primer pair. Movement of the sample from blister 264 to the second-stage blisters completes the PCR reaction mixture. Control samples from chamber 292l are also moved to control blisters 283 via channel 267. The control samples may be positive or negative controls, as desired. Illustratively, each pouch would contain control reactions that validate the operation of each step in the process and demonstrate that positive results are not the result of self-contamination with previously amplified nucleic acids. However, this is not practical in many protocols, particularly for a highly multiplexed reaction. One illustrative way of providing suitable controls involves spiking samples with a species such as baker's yeast. The nucleic acids are extracted from the yeast, alongside other nucleic acids. First- and second-stage PCR reactions amplify DNA and/or RNA targets from the yeast genome. Illustratively, an mRNA sequence derived from a spliced pre-mRNA can be used to generate an RNA-specific target sequence by arranging the primer sequences to span an intron. A quantitative analysis of the yeast copy number against reference standards allows substantial validation that each component of the system is working. Negative control reactions for each of the many second-stage assays are more problematic. It may be desirable to run control reactions either in parallel or in a separate run.

Activation of bladder 882 of bladder assembly 810 seals the samples into their respective second-stage blisters 282, 283, and activation of bladder 880 provides gentle pressure on second-stage blisters 282, 283, to force second-stage blisters 282, 283 into contact with a heater/cooler device. A window 847 positioned over the second-stage amplification zone 280 allows fluorescence monitoring of the array during PCR and during a DNA melting-curve analysis of the reaction products.

It is noted that the pouch 210 of FIG. 6 has several unsealed areas, such as unsealed area 255 and unsealed area 256. These unsealed areas form blisters that are not involved in any of the reactions in this illustrative embodiment. Rather, these unsealed areas are provided in space between the working blisters and channels. In some manufacturing processes, as compared to pouches that are sealed in all unused space, it has been found that fewer leaks sometimes result when unsealed areas such as 255 and 256 are provided, presumably by reducing problematic wrinkles in the film material. Such unsealed areas optionally may be provided on any pouch embodiment.

FIG. 8 shows an illustrative apparatus 800 that could be used with pouch 210. Instrument 800 includes a support member 802 that could form a wall of a casing or be mounted within a casing. Instrument 800 also includes a second support member 804 that is optionally movable with respect to support member 802, to allow insertion and withdrawal of pouch 210. Movable support member 804 may be mounted on a track or may be moved relative to support member 802 in any of a variety of ways. Illustratively, a lid 805 fits over pouch 210 once pouch 210 has been inserted into instrument 800. In another embodiment, both support members 802 and 804 may be fixed, with pouch 210 held into place by other mechanical means or by pneumatic pressure.

Illustratively, the bladder assembly 810 and pneumatic valve assembly 808 are mounted on movable member 802, while the heaters 886 and 888 are mounted on support member 802. However, it is understood that this arrangement is illustrative only and that other arrangements are possible. As bladder assembly 810 and pneumatic valve assembly 808 are mounted on movable support member 804, these pneumatic actuators may be moved toward pouch 210, such that the pneumatic actuators are placed in contact with pouch 210. When pouch 210 is inserted into instrument 800 and movable support member 804 is moved toward support member 802, the various blisters of pouch 210 are in a position adjacent to the various pneumatic bladders of bladder assembly 810 and the various pneumatic pistons of pneumatic valve assembly 808, such that activation of the pneumatic actuators may force liquid from one or more of the blisters of pouch 210 or may form pinch valves with one or more channels of pouch 210. The relationship between the blisters and channels of pouch 210 and the pneumatic actuators of bladder assembly 810 and pneumatic valve assembly 808 are discussed in more detail below with respect to FIGS. 9 and 10.

Each pneumatic actuator has one or more pneumatic fittings. For example, bladder 824 of bladder assembly 810 has pneumatic fitting 824a and pneumatic piston 843 has its associated pneumatic fitting 843a. In the illustrative embodiment, each of the pneumatic fittings of bladder assembly 810 extends through a passageway 816 in movable support member 804, where a hose 878 connects each pneumatic fitting to compressed air source 895 via valves 899. In the illustrative embodiment, the passageways 816 not only provide access to compressed air source 895, but the passageways also aid in aligning the various components of bladder assembly 810, so that the bladders align properly with the blisters of pouch 210.

Similarly, pneumatic valve assembly 808 is also mounted on movable support member 804, although it is understood that other configurations are possible. In the illustrative embodiment, pins 858 on pneumatic valve assembly 808 mount in mounting openings 859 on movable support member 804, and pneumatic pistons 843, 852, 853, and 862 extend through passageways 816 in movable support member 804, to contact pouch 210. As illustrated, bladder assembly is mounted on a first side 811 of movable support member 804 while pneumatic valve assembly 808 is mounted on a second side 812 of movable support member 804. However, because pneumatic pistons 843, 852, 853, and 862 extend through passageways 816, the pneumatic pistons of pneumatic valve assembly 808 and the pneumatic bladders of bladder assembly 810 work together to provide the necessary pneumatic actuators for pouch 210.

As discussed above, each of the pneumatic actuators of bladder assembly 810 and pneumatic valve assembly 808 has an associated pneumatic fitting. While only several hoses 878 are shown in FIG. 8, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention.

Several other components of instrument 810 are also connected to compressed gas source 895. Magnet 850, which is mounted on a first side 813 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 246 of pouch 210. However, depending on the material of support member 802, it is understood that recess 851 need not extend all the way through support member 802, as long as when magnet 850 is deployed, magnet 850 is close enough to provide a sufficient magnetic field at blister 246, and when magnet 850 is retracted, magnet 850 does not significantly affect any magnetic beads present in blister 246. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required.

The various pneumatic pistons 868 of pneumatic piston array 869, which is mounted on support 802, are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown. When the pouch 210 is inserted into instrument 800, the twelve pneumatic pistons 868 are positioned to activate their respective twelve plungers 268 of pouch 210. When lid 805 is closed over pouch 210, a lip 806 on lid 805 provides a support for fitment 290, so that as the pneumatic pistons 868 are activated, lid 805 holds fitment 290 in place. It is understood that other supports for fitment 290 are within the scope of this invention.

A pair of heating/cooling devices, illustratively Peltier heaters, are mounted on a second side 814 of support 802. First-stage heater 886 is positioned to heat and cool the contents of blister 264 for first-stage PCR. Second-stage heater 888 is positioned to heat and cool the contents of second-stage blisters 282 and 283 of pouch 210, for second-stage PCR. It is understood, however, that these heaters could also be used for other heating purposes, and that other heaters may be included, as appropriate for the particular application.

If desired, a feedback mechanism (not shown) may be included in instrument 800 for providing feedback regarding whether the sample has actually been forced into a particular blister. Illustrative feedback mechanisms include temperature or pressure sensors or optical detectors, particularly if a fluorescent or colored dye is included. Such feedback mechanisms illustratively may be mounted on either of support members 802 or 804. For example, a pressure sensor may be mounted on support 802 adjacent the location of blister 264. When the sample is supposedly moved to blister 264, if the pressure sensor is depressed, then sample processing is allowed to continue. However, if the pressure sensor is not depressed, then sample processing may be stopped, or an error message may be displayed on screen 892. Any combination or all of the blisters may have feedback mechanisms to provide feedback regarding proper movement of the sample through the pouch.

When fluorescent detection is desired, an optical array 890 may be provided. As shown in FIG. 8, optical array 890 includes a light source 898, illustratively a filtered LED light source, filtered white light, or laser illumination, and a camera 896. A window 847 through movable support 804 provides optical array 890 with access to second-stage amplification zone 280 of pouch 210. Camera 896 illustratively has a plurality of photodetectors each corresponding to a second-stage blister 282, 823 in pouch 210. Alternatively, camera 896 may take images that contain all of the second-stage blisters 282, 283, and the image may be divided into separate fields corresponding to each of the second-stage blisters 282, 283. Depending on the configuration, optical array 890 may be stationary, or optical array 890 may be placed on movers attached to one or more motors and moved to obtain signals from each individual second-stage blister 282, 283. It is understood that other arrangements are possible.

As shown, a computer 894 controls valves 899 of compressed air source 895, and thus controls all of the pneumatics of instrument 800. Computer 894 also controls heaters 886 and 888, and optical array 890. Each of these components is connected electrically, illustratively via cables 891, although other physical or wireless connections are within the scope of this invention. It is understood that computer 894 may be housed within instrument 890 or may be external to instrument 890. Further, computer 894 may include built-in circuit boards that control some or all of the components, and may also include an external computer, such as a desktop or laptop PC, to receive and display data from the optical array. An interface 893, illustratively a keyboard interface, may be provided including keys for inputting information and variables such as temperatures, cycle times, etc. Illustratively, a display 892 is also provided. Display 892 may be an LED, LCD, or other such display, for example.

Figure 9:
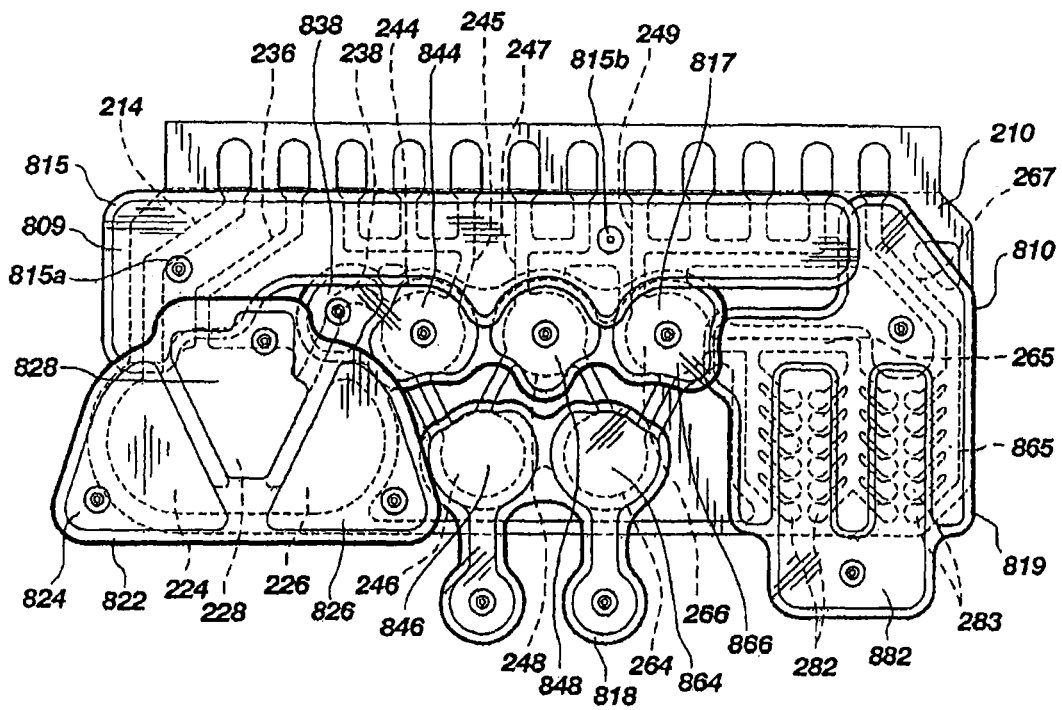
FIG. 9 shows a partial cross-sectional view of the instrument of FIG. 8, including the bladder components of FIG. 7, with the pouch of FIG. 6 shown in shadow.

FIG. 9 shows the relationship between bladder assembly 810 and pouch 210 during operation of instrument 800. Bladder assembly comprises sub-assemblies 815, 817, 818, 819, and 822. Because bladder 809 of bladder sub-assembly 815 is large, bladder sub-assembly 815 illustratively has two pneumatic fittings 815a and 815b. Bladder 809 is used to close off chambers 292 (as shown in FIG. 6) from the plastic film portion 217 of pouch 210. When one of the plungers 268 is depressed, one or both of pneumatic fittings 815a and 815b permit bladder 809 to deflate. After the fluid from one of the chambers 292 passes through, bladder 809 is re-pressurized, sealing off channels 214, 236, 245, 247, and 249. While illustrative bladder sub-assembly 815 has only one bladder 809, it is understood that other configurations are possible, illustratively where each of channels 214, 236, 245, 247, and 249 has its own associated bladder or pneumatic piston. Bladder sub-assembly 822 illustratively comprises three bladders 824, 826, and 828. As discussed above, bladders 824, 824, and 828 drive the three-lobed blister 222 for cell lysis. As illustrated, bladders 824, 826, and 828 are slightly larger than their corresponding blisters 224, 226, 228. It has been found that, upon inflation, the surface of the bladders can become somewhat dome-shaped, and using slightly oversized bladders allows for good contact over the entire surface of the corresponding blister, enabling more uniform pressure and better evacuation of the blister. However, in some circumstances, complete evacuation of individual blisters may or may not be desired, and larger or smaller-sized bladders may be used to control the blister volume evacuated. Bladder sub-assembly 817 has four bladders. Bladder 836 functions as a pinch-valve for channel 236, while bladders 844, 848, and 866 are configured to provide pressure on blisters 244, 248, and 266, respectively. Bladder sub-assembly 818 has two bladders 846 and 864, which are configured to provide pressure on blisters 246 and 264, respectively. Finally, bladder sub-assembly 819 controls second-stage amplification zone 280. Bladder 865 acts as a pinch valve for channels 265 and 267, while bladder 882 provides gentle pressure to second-stage blisters 282 and 283, to force second-stage blisters into close contact with heater 888. While bladder assembly 810 is provided with five sub-assemblies, it is understood that this configuration is illustrative only and that any number of sub-assemblies could be used or that bladder assembly 810 could be provided as a single integral assembly.

Figure 10:
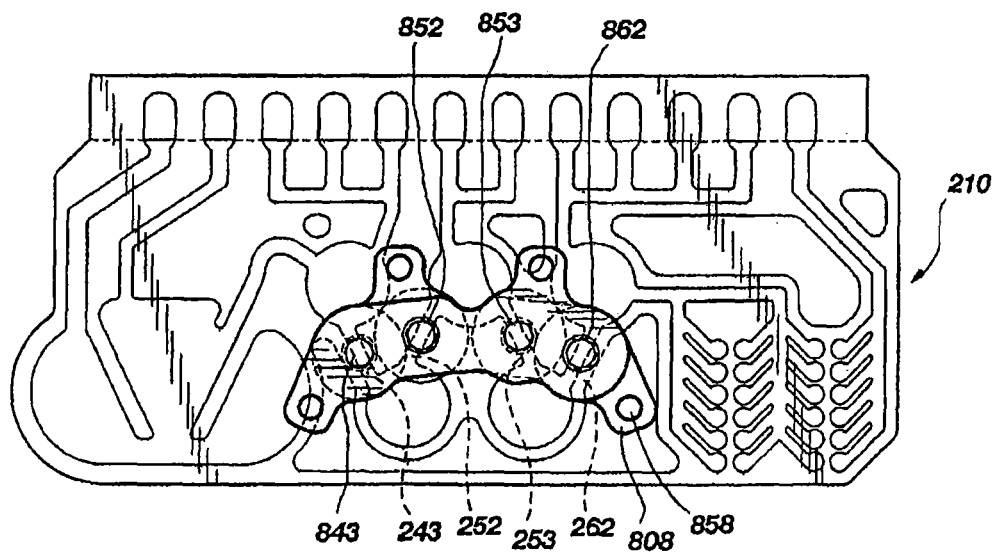
FIG. 10 shows a partial cross-sectional view of the instrument of FIG. 8, including various bladders for pinch valves and the pouch of FIG. 6.

FIG. 10 similarly shows the relationship between pneumatic valve assembly 808 and pouch 210 during operation of instrument 800. Rather than bladders, pneumatic valve assembly 808 has four pneumatic pistons 842, 852, 853, and 862. These pneumatic pistons 842, 852, 853, and 862, each driven by compressed air, provide directed pressure on channels 242, 252, 253, and 262. Because the pistons are fairly narrow in diameter, they can fit between bladder sub-assembly 817 and bladder sub-assembly 818 to provide pinch valves for channels 242, 252, 253, and 262, allowing channels 242, 252, 253, and 262 to be fairly short. However, if desired, pneumatic pistons 842, 852, 853, and 862 could be replaced by bladders, which may be included in bladder assembly 810, obviating the need for pneumatic valve assembly 808. It is understood that any combination of bladders and pneumatic pistons are within the scope of this invention. It is also understood that other methods of providing pressure on the channels and blisters of pouch 210, as are known in the art, are within the scope of this invention.

FIG. 15 shows a pouch 510 that is similar to pouch 210 of FIG. 6. Fitment 590, with entry channels 515a through 515l, is similar to fitment 290, with entry channels 215a through 215l. Blisters 544, 546, 548, 564, and 566, with their respective channels 538, 543, 552, 553, 562, and 565 are similar to blisters 244, 246, 248, 264, and 266, with their respective channels 238, 243, 252, 253, 262, and 265 of pouch 210. The channels 245, 247, and 249 of pouch 210 have been somewhat reconfigured as channels 545a-c, 547a-b, and 548a-c on pouch 510; the respective channels of 510 are somewhat shorter than their counterpart channels on pouch 210. However, it is understood that channel configurations are illustrative only, and that various channel configurations are within the scope of this invention.

There are two main differences between pouch 510 of FIG. 15 and pouch 210 of FIG. 6. First, three-lobed blister 222 has been replaced by lysis blister 522. Lysis blister 522 is configured for vortexing via impaction using rotating blades or paddles 21 attached to electric motor 19, as shown in FIG. 2b. Since this method of lysing does not rely on alternating pressure of pneumatic pistons, only a single-lobed blister is shown. Because lysis blister 522 has only a single lobe, both channels 514 and 536 lead to the single lobe of lysis blister 522. It is understood that lysis blister 522 may be used in any of the pouch embodiments described herein. It is further understood that lysis assembly 810 illustratively may be modified to replace bladders 824, 826, and 828 of bladder sub-assembly 822 with a single bladder configured for blister 522. Conversely, a three-lobed blister, as described in various other embodiments above, may be used in pouch 510. Lysis blister 522 may be provided with an optional reinforcing patch 523, illustratively attached using adhesive or lamination to the exterior surface of lysis blister 522. Reinforcing patch 523 aids in minimizing tearing of pouch 510 due to repeated contact by paddles 21. FIG. 15a shows an electric motor, illustratively a Mabuchi RC-280SA-2865 DC Motor (Chiba, Japan), mounted on second support member 804. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 21 are impacting pouch 510. Other voltages and speeds may be used for lysis depending on the motor and paddles used. Optionally, controlled small volumes of air may be provided into the bladder adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis.

The second main difference between pouch 510 of FIG. 15 and pouch 210 of FIG. 6 is that the blisters 281, 282, and 283 of second-stage amplification zone 280 have been replaced by high density array 581 in second-stage amplification zone 580. High density array 581 comprises plurality of second-stage wells 582, illustratively 50 or more wells, and even more illustratively 120 or more wells. Embodiments with more second-stage wells 582, illustratively about 200, about 400, or even about 500 or more are within the scope of this invention. Other configurations are within the scope of this invention as well. Additional second-stage wells 582 may be added by making wells 582 smaller, by making high density array 581 larger, or a combination thereof. For second-stage PCR, each of the wells may contain a pair of primers. It is understood that one or more wells may be used for positive or negative controls.

Cross-contamination between wells as the wells are filled with the diluted first-stage amplification product in blister 566 can be a major problem. Cross-contamination was controlled in pouch 210 by filling each second-stage blister through a separate branch of channel 265 and then sealing with bladder 882, illustrated in FIG. 9. With high density array 581, wherein fluid may fill some or all of blister 584, cross-contamination between wells must also be controlled. In one embodiment, the second-stage PCR primers may be bound covalently or non-covalently to the inside surface of each well, thus functioning much like a PCR chip. However, in many embodiments it is desirable to control cross-contamination between wells without tethering the PCR primers to the wells. Controlling cross-contamination between wells can be difficult in an embodiment wherein the fluid from blister 566 is moved to wells 582 by flowing across a first surface 581*a* of high density array 581.

There are several desirable features for successful loading of the second-stage amplification zone 580. First, it is desirable that the incoming fluid from blister 566 fill substantially all of the wells 582 to substantially the same level. An unfilled well would produce a false negative signal. Second, it is desirable that the process of filling the wells 582 should not cause the primers in the well to leak out. Loss of primers from one well can limit the efficiency of the PCR reaction in that well and can contaminate neighboring wells. Third, after the wells 582 have been filled and PCR started, it is desirable that the wells be completely sealed from each other. Amplicon leakage out of one well and into another well can lower signal in the first well and raise signal in the second well, potentially leading to a false negative in the first well and a false positive in the second well. Further, for certain kinds of controls, it is important that amplicon generated in one well not enter another well where it can be further amplified.

Solutions to this problem include use of a barrier layer. In one example, the barrier layer is a physical barrier that is provided to allow for rapid loading of the wells and for rapid sealing from the bulk fluid. In another example, combined chemical and physical barriers are used, wherein the physical barrier is used to seal the wells and then the chemical barrier conditionally releases the oligonucleotide primers into the well solution, for example by heating, slow release, or enzymatic digestion. Well depth or channel length to each well also may be used to control release of the reagents from the wells. Other means for loading high density array 581 are possible.

Figure 16:
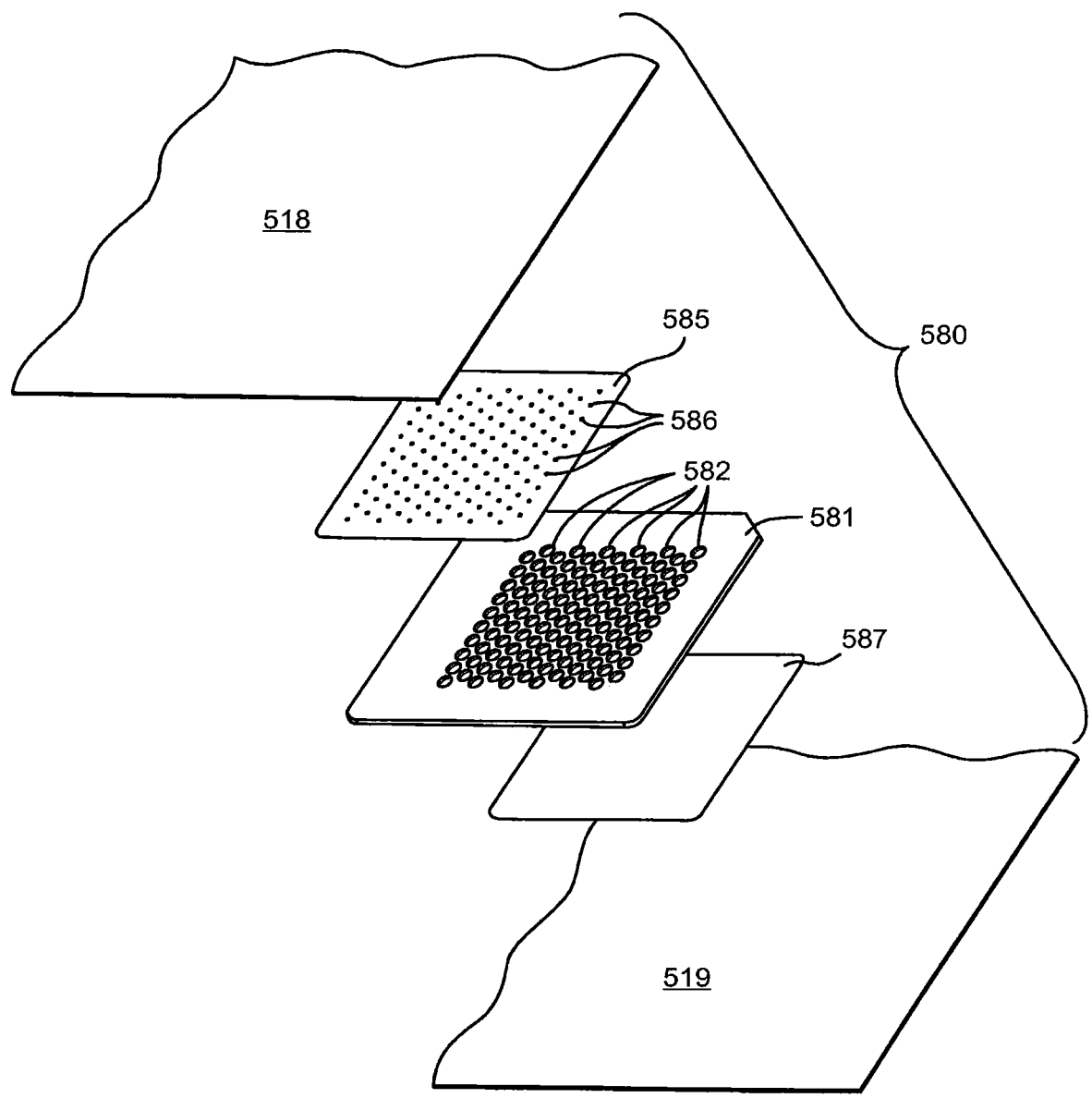
FIG. 16 is an exploded perspective view of the second-stage high density array of FIG. 15.
Figure 17:
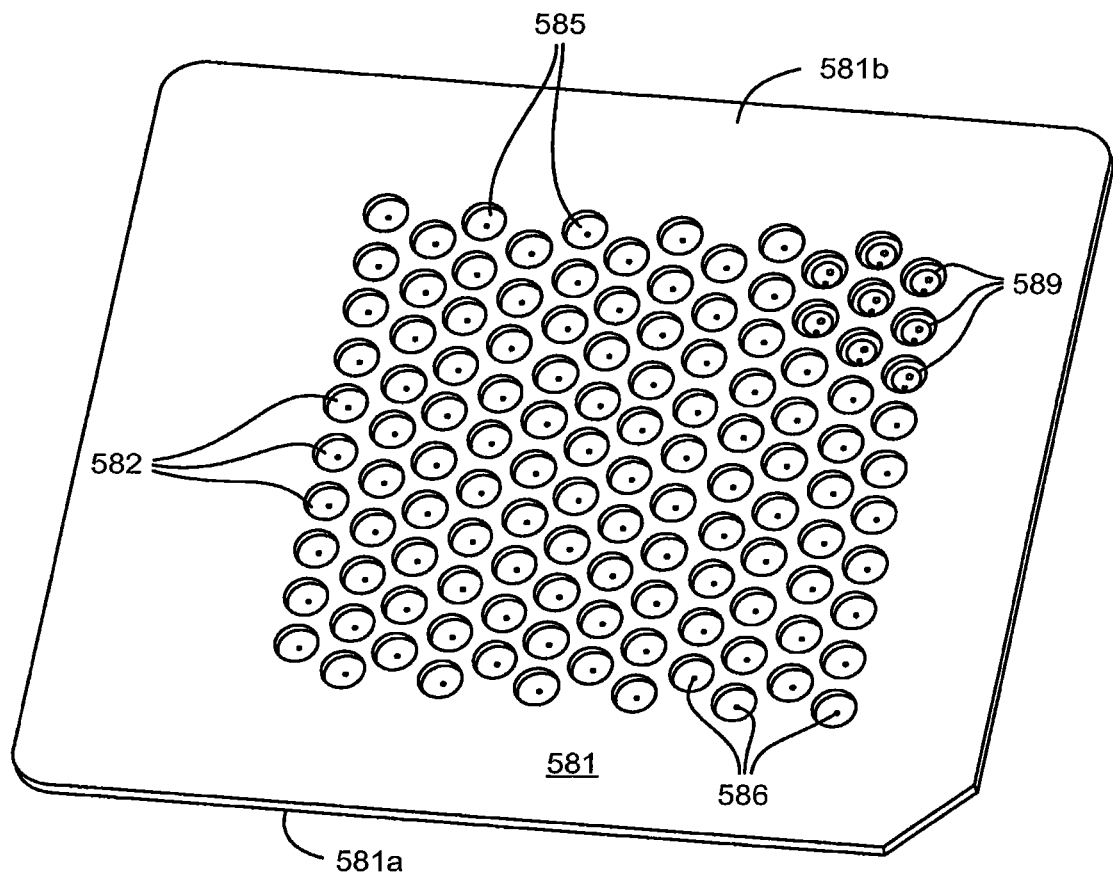
FIG. 17 is a bottom view of the second-stage high density array of FIG. 15, shown during construction of the second-stage high density array.

FIGS. 15-17 show an illustrative embodiment of second-stage 580 using a physical barrier. Sandwiched between first layer 518 and second layer 519 of pouch 510 is high density array 581, with wells 582. As best seen in FIG. 16, pierced layer 585, with piercings 586, is provided on one side of high density array 581 to act as the physical barrier, and a second layer 587, is provided on the opposite side of high density array 581 to form the bottom of wells 582. Illustratively, pierced layer 585 and second layer 587 are plastic films that have been sealed to high density array 581, illustratively by heat sealing, although it is understood that other methods of sealing may be employed. It is also understood that the material used for high density array 581 and the material used for pierced layer 585 and second layer 587 should be compatible with each other, with the sealing method, and with the chemistry being used. When used for PCR, examples of compatible plastics that can used for high density array 581 and can be heat-sealed are PE, PP, Monprene®, and other block copolymer elastomers. If fluorescent dyes are used in the detection chemistry, it may be desirable for high density array 581 to be formed from black or other relatively fluorescently opaque materials, to minimize signal bleed from one well 582 to its neighboring wells and for at least one of layers 585 and 587 to be relatively fluorescently transparent. For pierced layer 585 and second layer 587, laminates of a strong engineering plastic such as Mylar® or PET with heat-sealable plastic layers such as PE, PP and Dupont Surlyn® may be used. For adhesive-based systems, rigid engineering plastics such as PET or polycarbonate may be used to form high density array 581 and films of PCR-compatible plastics are then used as pierced layer 585 and second layer 587. In one illustrative embodiment, high density array 581 is formed of black PE, a composite polyethylene/PET laminate (or Xerox® PN 104702 hot laminating pouch material) is used for pierced layer 585 and second layer 587 which are heat sealed to high density array 581, and composite polypropylene/PET is used for first and second layers 518, 519 of pouch 510.

It is understood that piercings 586 align with wells 582. It is also understood that piercings 586 are small enough that, absent some force, fluid does not readily flow through piercings 586. Illustrative piercings may be 0.001-0.1 mm, more illustratively 0.005-0.02 mm, and more illustratively about 0.01 mm. In the illustrative embodiment, second-stage amplification zone 580 is provided under vacuum, such that when fluid is received from blister 566, the vacuum draws fluid through piercings 586 into each well 582. Once the wells 582 are filled, a force is no longer present to force fluid into or out of the wells 582. A bladder adjacent second-stage amplification zone 580 (not shown, but similar in position to bladders 880/882) may then be activated to press first layer 518 against high density array 581 and seal fluid into the wells 582. While first layer 518 of pouch 510 is used to seal the wells 582, it is understood that an optional sealing layer may be provided between pierced layer 585 and first layer 510.

In one illustrative example, second-stage amplification zone 580 may be prepared as follows. High density array 581 may be prepared by first punching, molding, or otherwise forming an array of wells 582 in a plastic sheet (illustratively 0.1 to 1 mm thick). The wells may form any regular or irregular array that is desired, and may have a volume illustratively of 0.05 µl to 20 µl, and more illustratively of 0.1 µl to 4 µl. One of layers 585 or 587 is then laminated to a first surface 581*a* of high density array 581, illustratively by heat or adhesive. As shown in FIG. 17, pierced layer 585 is applied to first surface 581*a*. Reagents 589, illustratively elements of the chemistry of the array that are unique, such as PCR primer pairs, are then spotted into the wells either manually by pipetting, or automatically (illustratively using x/y positionable spotters such as pin-spotters, dot-matrix printers, small-volume automatic pipettes, or micro-fluidic micro-contact spotters). After the reagents 589 have been dried in each well 582, the second of layers 585 or 587 is applied to the second surface 581*b* of array 581. Layer 585 is pierced using an array of small diameter needles to form piercings 586. Piercings 586 may be formed either before or after layer 585 has been fixed to array 581. It is understood that spotting can be done on either layer 585 before or after piercing or on layer 587. Spotting an array with holes pre-pierced has not shown to leak substantially and offers the advantage that the needles used for piercing are not contaminated by touching the spotted reagents. Alternatively, to minimize the possibility of leakage, and to position the spotted reagents at the most distant location in the array, it may be desirable to spot the reagents 589 onto second layer 587, seal the array 581 with layer 585, and then pierce layer 585. In an illustrative example, reagents are spotted onto second layer 587 using a GeSiM A060-324 Nano-Plotter 2.1/E (Grosserkmannsdorf, Germany). Using such a spotter, multiple arrays may be spotted simultaneously.

Once spotted and pierced, array 581 is placed inside layers 518 and 519 of pouch 510 and sealed in place, illustratively by either heat sealing, using an adhesive, ultrasonically welding, mechanical closure, or other means of enclosing array 581 inside pouch 510 within blister 584. It is understood that blister 584 is fluidly connected to blister 566 via channel 565, and that liquid can flow from channel 565 into blister 584 and over piercings 586. In one illustrative example, when blister 584 is formed, care is taken to allow a path for air to escape. This can be accomplished by "waffling" the inside surface of first layer 518 adjacent to second-stage amplification zone 580 to imprint the film material with a pattern of slightly raised texture. This allows air and liquid to pass along the surface of pierced layer 585, and better allows liquid to reach and fill all of wells 582. The pouch 510 is then placed inside a vacuum chamber and evacuated. Illustratively, when the pressure has reached approximately 0.3 millibars, a pneumatic cylinder inside the vacuum chamber is actuated, driving down a plunger into fitment 590 to seal channel 567, thereby cutting the path from the array inside the sealed pouch, and the vacuum chamber. A plurality of other plungers are also driven into fitment 590 to seal the various entry channels 515. The pouch is removed from the vacuum chamber and may be packaged for long-term storage in a vacuum-bag.

Pouch 510 may be used in a manner similar to pouch 210. Because array 581 is packaged in vacuum, when liquid is moved from blister 566 to second-stage amplification zone 580, the liquid sample is drawn through piercings 586 and into wells 582. Excess liquid is forced away by inflating a pneumatic bladder over the array and thermal cycling is accomplished as described above, illustratively by heating and cooling a Peltier element pressed against one side of the array.

As mentioned above, pierced layer 585 may be replaced by a variety of suitable physical or chemical barriers. In one illustrative embodiment using a chemical barrier, pierced layer 585 is omitted, and reagents 589 are spotted into wells 582 in a buffer that dissolves relatively slowly. Illustratively, reagents 589 that contain polymers such as PEG, Ficoll or polysorbate 20 or sugars such as sucrose, trehalose or mannitol in appropriate concentrations will be compatible with the second-stage PCR reaction and may dissolve more slowly than primers spotted solely in water or Tris/EDTA. The primers spotted in one of these buffers may be air dried into the wells 582, as described above (it is understood that in such an embodiment, second layer 587 is affixed to high density array 581 for spotting). These same polymers may be used in lyophilization of enzyme reagents (e.g. the enzymes and buffers used in PCR) to form an open matrix containing the stabilized enzymes. Thus, the primers spotted in these buffers can be lyophilized in place in the wells 582, leading to slower but potentially more complete rehydration than with air drying. When pouch 510 is used, the fluid from blister 566 is driven into the well by vacuum or pressure and starts to dissolve the primer mix. By selecting a buffer that dissolves suitably slowly, when the bladder adjacent second-stage amplification zone 580 is actuated, the contents of each well 582 is sealed therein prior to any substantial cross-contamination.

Another embodiment uses a matrix that does not dissolve until second-stage amplification zone 580 is heated above a predetermined temperature. One example of such a matrix is low melt agarose such as GenePure LowMelt Agarose (ISC Bioexpress). In one example, a 1.5% solution of this agarose melts at 65° C. and gels at 24-28° C. Prior to spotting, reagents 589 illustratively may be warmed to 50° C. and mixed with this agarose that had already been melted and then spotted into wells 582 in a small volume (illustratively 100 to 500 nl). To keep the mixture liquid during spotting, this may have to be done in a cabinet heated above the melting temperature of the agarose. Alternatively, it may be possible to pipette dilute solutions of the agarose without melting. After the agarose/reagent mixture is spotted, the high density array 581 is dried. This can be a simple air drying or the primer-agarose mixture can contain the sugars and polymers listed above so that the reagents can be freeze dried. When pouch 510 is used for PCR, second-stage amplification zone 580 may be heated, illustratively to 55° C., as the fluid from blister 566 is moved into high density array 581. At this temperature, the agarose does not melt so the primers are not released into solution. Once high density array 581 is filled, the corresponding bladder is inflated to seal the wells. When the temperature rises above 65° C. in the first denaturation step of the first PCR cycle, the agarose containing the primers melts, releasing the primers into the master mix. Illustratively, thermal cycling never goes below 60° C. (or other melting temperature for the agarose) so that the agarose does not gel during thermal cycling. Furthermore, in the illustrative instrument 800 of FIG. 8, the repeated temperature cycling is driven by heater 888, which is located on one side of the pouch. It is expected that there will often be a temperature gradient across the PCR solution in wells 582, which should facilitate mixing of the primers by convective fluid flow. Wax may also be used in a similar embodiment.

In a further embodiment, the primers may be conditionally bound to the wells 581, with subsequent releasing of the primers into solution after the wells 581 have been filled. Depending upon how the primers are attached to the plastic substrate, the primers may be cleaved using heat (illustratively during the first cycle of the PCR reaction), light (illustratively irradiating through window 847), chemicals (e.g. dithiothreitol together with heat will reduce disulfide bonds that may be used to link primers to the wells), or enzymes (e.g. site specific proteases such at Tissue Plasminogen Activator can be used to cleave the proper peptide linker attaching primers to the substrate).

In yet another embodiment, a DNase may be injected into second-stage amplification zone 580 subsequent to amplification, to minimize further any potential risk of contamination.

It is understood that second-stage amplification zone 580 has been described herein for use with PCR. However, other uses for pouch 510 and second-stage amplification zone 580 are within the scope of this invention. Further, it is understood that second-stage amplification zone 580 may be used with or without nucleic acid extraction and a first stage PCR amplification zone. Finally, it is understood that second-stage amplification zone 580 may be used with any of the pouch embodiments described herein.

Example 1: Nested Multiplex PCR

A set of reactions was run in a pouch 110 of FIG. 5, on an instrument similar to instrument 800 but configured for pouch 110. To show cell lysis and effectiveness of the two-stage nucleic acid amplification, 50 µL each of a live culture of S. cerevisiae and S. pombe at log phase was mixed with 100 µL of a nasopharyngeal aspirate sample from a healthy donor to form the sample, then mixed with 200 µL lysis buffer (6M guanidine-HCl, 15% TritonX 100, 3M sodium acetate. 300 µL of the 400 µL sample in lysis buffer was then injected into chamber 192a of pouch 110.

The pouch 110 was manufactured with 0.25 g ZS beads sealed in three-lobed blister 122. Second-stage primers, as discussed below, were also spotted in blisters 181 and 182 during manufacture of pouch 110. The pouch 110 was loaded as follows:

115a sample and lysis buffer, as described above,
115b magnetic beads in the lysis buffer,
115d-e wash buffer (10 mM sodium citrate),
115g elution buffer (10 mM Tris, 0.1 mM EDTA)
115h first-stage PCR buffer:
 0.2 mM dNTPs
 0.3 µM each primer:
  Sc1: primers configured for amplifying a portion of the YRA1 nuclear protein that binds to RNA and to MEX67p of S. cerevisiae. The primers are configured to amplify across an intron such that amplification of cDNA (mRNA reverse-transcribed via M-MLV) yields a 180 bp amplicon.
  Sc2: primers configured for amplifying a 121 bp region of the cDNA of MRK1 glycogen synthase kinase 3 (GSK-3) homolog of S. cerevisiae.
  Sc3: primers configured for amplifying a 213 bp region of the cDNA of RUB1 ubiquitin-like protein of S. cerevisiae.
  Sp1: primers configured for amplifying a 200 bp region of the cDNA of suc1-cyclin-dependent protein kinase regulatory subunit of S. pombe.
  Sp2: primers configured for amplifying a 180 bp region of the cDNA of sec14-cytosolic factor family of S. pombe.
 PCR buffer with 3 mM MgCl$_2$ (without BSA)
 50 units M-MLV
 4.5 units Taq:Antibody
 100 units RNAseOut
115j-k second-stage PCR buffer
 0.2 mM dNTPs
 1×LC Green Plus (Idaho Technology)
 PCR buffer with 2 mM MgCl$_2$ (with BSA),
 4.5 units Taq
115l—second-stage PCR buffer with a sample of the first-stage amplicons.

During manufacture, second-stage blisters 181 and 182 were spotted with nested second-stage primers. Each blister was spotted with one primer pair in an amount to result in a final concentration of about 0.3 µM once rehydrated with the second-stage PCR buffer. The second-stage nested primers are as follows:

Sc1: primers configured for amplifying an 80 bp fragment of the Sc1 cDNA first-stage amplicon.
Sc2: primers configured for amplifying a 121 bp fragment of the Sc1 cDNA first-stage amplicon.
Sc3: primers configured for amplifying a 93 bp portion of the Sc1 cDNA first-stage amplicon.
Sp1: primers configured for amplifying a 99 bp portion of the Sc1 cDNA first-stage amplicon.
Sp2: primers configured for amplifying a 96 bp portion of the Sc cDNA first-stage amplicon.

There is no overlap between the first-stage and second stage primer pairs for any of the targets. Each pair of primers was spotted into one negative control blister 181 and two second-stage blisters 182, so that each second-stage amplification would be run in duplicate, each duplicate with a negative control.

After loading, activation of the plunger associated with entry channel 115a moved the sample to three-lobed blister 122, activation of the plunger associated with entry channel 115b moved the magnetic beads to reservoir 101, activation of the plungers associated with entry channels 115d-e moved wash buffer to reservoirs 102 and 103, activation of the plunger associated with entry channel 115g moved elution buffer to reservoir 104, activation of the plunger associated with entry channel 115h moved first-stage PCR buffer to reservoir 105, activation of the plungers associated with entry channels 115j-k moved second stage PCR buffer to reservoirs 106 and 107, and activation of the plunger associated with entry channel 115l moved the positive control (second-stage PCR buffer with a sample of previously prepared first-stage amplicon) to reservoir 108. In this present example, the plungers associated with entry channels 115a and 115b were depressed prior to loading the pouch 110 into the instrument. All other plungers were depressed sequentially in the instrument during the run, and fluids were moved to reservoirs 102 through 108 as needed.

Once pouch 110 was placed into the instrument, and beating took place for ten minutes in the presence of ZS beads, as described above. Once cell lysis was complete, reservoir 101 was compressed and nucleic acid binding magnetic beads from reservoir 101 were forced into three-lobed blister 122, where the beads were mixed gently and allowed to incubate for 5 minutes.

The sample-bead mixture was then moved to blister 144, where the magnetic beads were captured via activation of the magnet. Once the magnet was deployed, bladders adjacent blister 144 were pressurized to force fluids back to three-lobed blister 122. The captured beads were then washed as described above, using the wash solution from reservoirs 102 and 103. Following washing, the beads were once again captured in blister 144 via activation of the magnet, and the elution buffer stored in reservoir 104 is moved to blister 144, where, after a 2 minute incubation, the nucleic acids eluted from the beads are then moved to blister 161, as discussed above.

In blister 161, the nucleic acid sample is mixed with first-stage PCR master mix from reservoir 105. The sample is then held at 40° C. for 10 minutes (during which time M-MLV converts mRNA to cDNA), then 94° C. for 2 minutes (to inactivate the M-MLV and remove antibody from taq). Thermal cycling is then 20 cycles of 94° C. for 10 second and 65° C. for 20 seconds.

Subsequent to first-stage amplification, the sample is diluted approximately 100-fold using the second-stage PCR master mix from reservoir 106. The sample is then moved to blisters 182, which were previously spotted with the second-stage primers, as discussed above. Second-stage PCR buffer was moved from reservoir 181 to negative control blisters 181, and the positive control mixture was moved to blisters 183 from reservoir 108. The samples were denatured for 30 seconds at 94° C., then amplified for 45 cycles of 94° C. for 5 seconds and 69° C. for 20 seconds.

Figure 13:
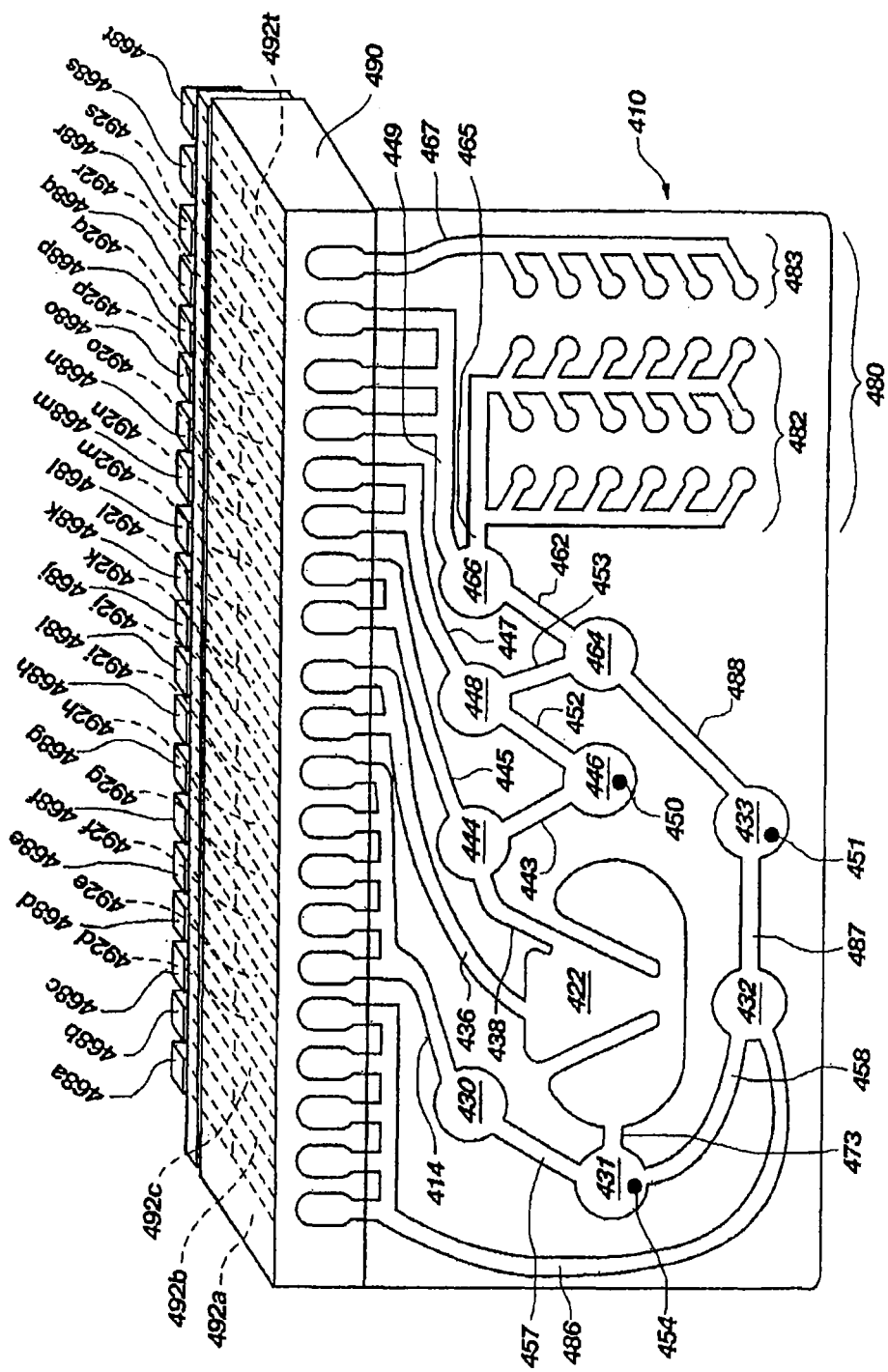
FIG. 13 is similar to FIG. 6, except showing a pouch configured for both PCR and immuno-PCR.
Figure 14:
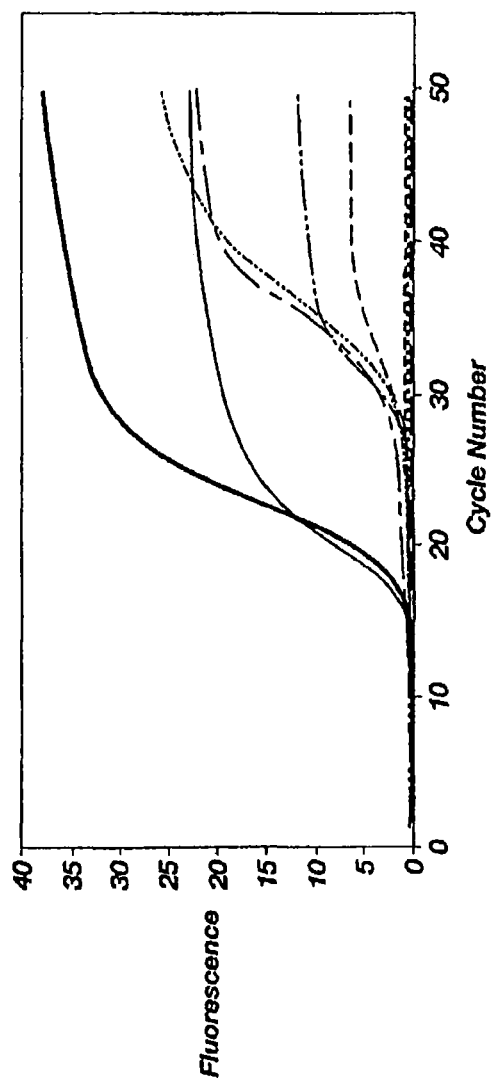
FIG. 14 shows amplification curves from second-stage amplification of a sample that was lysed and amplified in a pouch of FIG. 5 (- - - positive control; - - - S. cerevisiae target 1; S. cerevisiae target 2; - S. cerevisiae target 3; - - - - - - S. pombe target 1; - - - S. pombe target 2; - - - - negative controls).

As can be seen in FIG. 13, all target amplicons and the positive control showed amplification, while none of the negative controls showed amplification. Each sample was run in replicates. The replicates each showed similar amplification (data not shown).

It is understood that the S. cerevisiae and S. pombe targets are illustrative only and that other targets are within the scope of this invention.

Example 2: High Density PCR

The above example uses pouch 110 of FIG. 5. Pouch 110 has five negative control blisters 181, five positive control blisters 183, and ten low volume sample blisters 182. Pouch 210 of FIG. 6 increased the number of low volume sample blisters 282 to 18. However, high density array 581 of pouch 510, shown in FIG. 15 can have 120 or more second-stage wells 582. This increase in the number of second-stage reactions enables a wide set of potential diagnostic and human identification applications without the need to increase the size of the pouch and its instrument. Various examples are described herein.

In one example, it is known that standard commercial immunofluorescence assays for the common respiratory viruses can detect seven viruses: Adenovirus, PIV1, PIV2, PIV3, RSV, Influenza A, and Influenza B. A more complete panel illustratively would include assays for additional five viruses: coronavirus, human metapneumovirus, BOCAvirus, Rhinovirus and non-HRV Enterovirus. For highly variable viruses such as Adenovirus or HRV, it is desirable to use multiple primers to target all of the branches of the virus' lineage (illustratively 4 outer and 4 inner primer sets respectively). For other viruses such as coronavirus, there are 4 distinct lineages (229E, NL63, OC43, HKU1) that do not vary from one season to another, but they have diverged sufficiently enough that separate primer sets are required. The illustrative complete respiratory virus panel would also target the SARS coronavirus, possibly the avian influenza HA and N subtypes, and possibly others. Finally, some of the respiratory viruses show such a high rate of sequence variation that it would be beneficial to create more than one nested PCR assay for each such virus, thereby minimizing the chance of false negative results due to sequence variation under the primers. When all of the primer sets described herein are included, such a respiratory virus panel could have 80 or more specific amplicons in the second-stage amplification. The high density array 581 could easily accommodate such a panel in a single pouch 510.

A second application of the high density array 581 of pouch 510 would be to determine the identity and the antibiotic resistance spectrum of the multi-drug resistant bacteria isolated from infected patients. Current methods require several days to culture the organism and empirically test individual drug resistance profiles. During the time it takes to receive the results, physicians will often administer broad-spectrum antibiotics, which leads to an increase in multi-drug resistant bacteria. PCR primers have been developed to detect the genetic determinants of antibiotic resistance (the antibiotic resistance genes themselves). However because of the large number of variants of some of these genes, a large number of amplicons is required for a complete determination of the resistance profile. Hujer et. al. describe a panel of 62 PCR assays to identify the resistance genes present in *Acinetobacter* isolates. Again, the high density array 581 could easily accommodate such a panel in a single pouch.

A third example of the utility of the high density array is in the field of human identification, illustratively for forensic identification of human remains and for paternity testing. Most of the market in human identification is dominated by systems that analyze short tandem repeat sequences (STRs). This analysis has generally required separating the repeats by size, using e.g. capillary electrophoresis. The specialized laboratory equipment used for this purpose has generally not been field portable. There is growing interest in using Single Nucleotide Polymorphisms (SNPs) for identity testing, as there are a large set of techniques for identifying SNPs and some of these are amenable to field use. Sanchez et al. have published a set of 52 well-characterized SNPs that collectively give a very low probability of matching two individuals by chance (a mean match probability of at least $5.0 \times 10^{-19}$). In practice, it may take two amplicons for each SNP to accurately type each locus (see, e.g., Zhou et al.). Thus one pouch 510 with 104 second-stage wells 582 could completely type an individual at all of the 52 SNP loci.

It is understood that there are cost and workflow advantages gained by combining assays from different diagnostic applications into one pouch. For example the complete respiratory virus panel could be combined with the bacterial identification panel. These combinations could simplify manufacturing, since there are fewer types of pouches to assemble. They could also simplify the work of the end user, as there are fewer specific types of pouches that need to be stocked in a clinic, and also reducing the chance of using the wrong pouch for a particular clinical sample. For some applications, these advantages could offset an increase cost of manufacturing the pouch having a greater number of primer pairs. Thus one pouch 510 with 100 or more second-stage wells 582 could be used to accommodate multiple panels of assays.

Example 3: Process Controls

Controls for highly multiplexed assays can be problematic, especially in clinical diagnostic settings where quality must compete with cost per test. The high-density array 582 of pouch 510 potentially increases this problem because of the increased number of diagnostic targets that can be assayed in a single run. Various types of controls are discussed herein.

Illustrative process controls include mixing an intact organism, for example an organism containing an RNA target, into the patient sample before injecting the sample into the pouch. Such a target could be an intact RNA bacteriophage (MS2 or Qβ) or an intact plant RNA virus (Tobacco Mosaic Virus) or an mRNA present in an intact yeast. Outer primers specific for the RNA target would be present in the first-stage PCR and a well 582 containing the inner primers would be present in the high density array. Detection of amplification product in this well 582 confirms that all of the steps of the process are working correctly. A post-second-stage amplification melt curve could also be used to verify that the correct specific product was made. The crossing point ("Cp") determined from an amplification curve could be used to give a quantitative measure of the integrity of the reagents. For example the Cp can be compared to that of other pouches from the same lot run at a different time. While an intact organism is used, it is understood that purified or isolated nucleic acids may be used if it is not important to test for lysis. In other situations, it may be desirable to use the control to test only the later steps of the analysis. For example, spiking a natural or synthetic nucleic acid template into a well in the high density array along with the cognate primers could be used to test the second-stage PCR reaction, and spiking a nucleic acid template into the first-stage PCR with the appropriate primers in the first-stage PCR amplification mixture and in a well 582 of the second-stage amplification zone will test both the first- and second-stage PCR reactions.

Process controls such at described above do not test the integrity of the primers specific to the target amplicons. One example of a positive control that tests the integrity of the specific primers uses a mixture of nucleic acids, illustratively synthetic RNAs, as stability and variability often can be better controlled and these sequences cannot be present due to environmental contamination, wherein the mixture contains a nucleic acid for each of the primers present in the particular pouch. In a diagnostic setting, this positive control could be used at the end of a run of pouches used to test patient samples. The mixture is injected into a pouch, illustratively from the same lot as those used for the patient samples, and success is defined by all of the target amplicons providing a positive result. Negative controls can be done in the same way; at the end of a run of pouches used to test patient samples, water or buffer could be injected into a pouch and success defined by all of the target amplicons providing a negative result.

Individual workflow and protocols in a diagnostic lab may be used to determine the number of patient sample pouches run before the control pouches described above are run. Regardless of how frequently or infrequently the control pouches are run, these controls add to the time and cost of the total system. For this reason, it would be useful to make the controls internal to the pouch. The structure of the high density array 581 allows for the following novel approach to negative controls. In this example, a nucleic acid, illustratively a synthetic amplicon, is spiked into one of the wells 582a of the high density array 581. Primers to amplify this sequence are spiked into this well 582a and into two other wells 582b and 582c spaced across the array. Illustratively, the amplicon sequence and primers are artificial and designed so that none of the primers used will amplify another target by chance.

When a clean, uncontaminated pouch 510 is run in instrument 800, the well 582a containing the synthetic target will generate amplicon and therefore be called positive. The two other wells 582a, 582b that contain the corresponding primers should not amplify anything in the sample and thus be called negative. Pouch 510 may be treated further, for additional controls. Illustratively, bladder 880/882 holding the high density array against heater 888 is then depressurized and the contents of the wells 582 are mixed. In one illustrative method, the contents of the wells 582 are mixed as follows: heater 888 is used to cycle the temperature of the high density array above and below the boiling point of the buffer for a short time (for example three cycles of 85° C. for 10 sec then 105° C. for to 20 sec). Bubbles of steam generated in the wells 582 of high density array 581 should force the contents of wells 582 out into the second-stage amplification zone blister 580. Optionally, the contents of the second-stage amplification zone 580 may be mixed with the contents of rest of the pouch 510 by using the bladders to move liquid from one end of the pouch 510 to the other. The purpose of these steps is to mix the specific contamination control amplicon, along with any specific target amplicons throughout the pouch.

If the user accidentally opens a pouch after it has been run in this fashion, then both specific target amplicons and the contamination control amplicon will be released. If trace amounts of these nucleic acids contaminate a later pouch run, the instrument may detect the contamination event, as the wells 582b, 582c that contained only the primers specific for the synthetic amplicon will score positive. Software in the instrument will alert the user and the results of the run will be flagged as suspect.

In another method to control contamination, at the end of a run, a DNA degrading chemical or enzyme may be added to destroy substantially all of the DNA products of the first- and second-stage PCR reactions. Illustratively, this can be done in a way similar to the contamination detection method described above, by heating the contents of the second-stage array to above the local boiling temperature, thus drawing the amplified sample out of the wells 582 of the array 851, mixing the heated liquid with the diluted contents of the $1^{st}$ stage reaction, adding an aliquot of a DNA degrading substance, illustratively through entry channel 515k, either with or without cooling the mixture, and allowing the DNA degrading reaction to incubate until substantially all of the DNA produced in the PCR reaction has been destroyed. This can be accomplished using DNAases, acids, or oxidants, as are known in the art.

It is understood that any of the contamination controls described herein may be used independently or in any combination thereof.

Example 4: iPCR

In another example, the pouches and instruments of the present invention may be used for immuno-PCR (iPCR). iPCR combines the antibody specificity of ELISA with the sensitivity and multiplex capabilities of PCR. While iPCR has been applied to diagnostics and toxin detection, iPCR has not enjoyed widespread commercial application, presumably because PCR template contamination issues are severe in an open ELISA format. Because the pouch format of the present invention provides a sealed environment, the pouches of the present invention may be well suited for iPCR.

Figure 11:
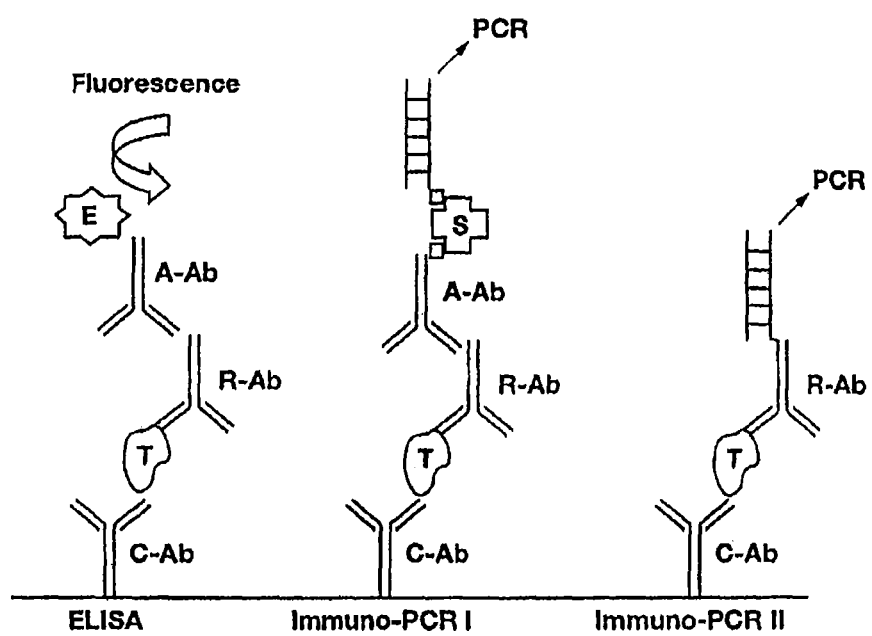
FIG. 11 shows schemes for ELISA and immuno-PCR, secondary antibody (A); capture antibody (C); enzyme (E); reporter antibody (R); bi-functional binding moiety (S) and antigen (T).

A traditional ELISA detection scheme is shown in FIG. 11 (labeled "ELISA"). In 1992, Cantor and colleagues (Sano, T., et al, Science, 1992. 258(5079): p. 120-2, herein incorporated by reference) described a modification of the basic ELISA technique (FIG. 11, similar to the "Immuno-PCR I" scheme without capture antibody C-Ab), in which the enzyme used for generating a specific signal is replaced by a unique DNA fragment indirectly attached to the reporter antibody R through a bi-functional binding moiety S, such as a streptavidin-protein A chimera. The DNA fragment is subsequently detected by PCR. It is known that PCR detection can provide dramatic increases in immuno-PCR assay sensitivity over corresponding ELISA assays, with improvements to sensitivity commonly $10^2$ to $10^4$-fold. Advances in quantitative real-time PCR methods have improved the speed and quantification of immuno-PCR. Direct coupling of the reporter antibody (R-Ab) with DNA template tags (FIG. 11, "Immuno-PCR II" scheme) has further increased the assay sensitivity 102 to 1 fold and made possible the development of multiplex immuno-PCR assays, in which each different antibody is tagged with a different oligonucleotide and, thus, each antigen is associated with a unique amplification product.

Despite these advantages over traditional ELISAs, iPCR has not been widely adopted in commercial products in the 13 years since it was first described. This is due in part to the contamination hazards inherent in any open-tube PCR analysis method. Prior art iPCR protocols are derived from ELISA assays and require numerous wash steps that increase the likelihood of contaminating the work area with amplified material. The significant risk of false positives due to workflow contamination has contributed to the avoidance of iPCR in diagnostic assessment.

Amplicon contamination issues slowed the widespread adoption of PCR itself in the diagnosis of human genetic conditions or of infectious disease until homogenous (i.e. "closed-tube") PCR assays were developed. By making the readout of the assay possible in a closed-tube system, spread of amplicon is severely curtailed. Similarly, iPCR may be more widely adopted if a closed system format were available. In the present system, the sample would be injected into a pouch that would be provided with all required reagents. The steps of antigen capture, wash, reporter-antibody binding, wash, and subsequent PCR detection could be performed completely within the pouch. Illustratively, nucleic acids would never leave the pouch and would be disposed of along with the pouch.

Any of the pouches of the present invention may be adapted for iPCR. For example, the pouch 210 of FIG. 6 illustratively may be adapted as follows. Chambers 292*a* through 292*l* would be filled with the following components. The sample illustratively comprising an unpurified and/or unmodified antigen (e.g. a toxin) is injected through injection port 241*a* to chamber 292*a*. A capture antibody conjugated to magnetic beads (C-Ab) is provided in chamber 292*b*. If multiple targets are to be tested, it is understood that multiple capture antibodies having specificity for multiple antigens may be used. An optional pre-wash buffer is provided in chamber 292*c*. A reporter antibody conjugated to an oligonucleotide template (R-Ab-DNA) is provided in chamber 292*d*. It is understood that the capture and reporter antibodies may be monoclonal or polyclonal. When multiple antigens are to be detected, the capture and reporter antibodies may contain only polyclonal antibodies, only monoclonal antibodies, or any combination of polyclonals specific for one antigen and monoclonals specific for another antigen. When a reporter antibody is polyclonal, it is understood that all reporter antibodies having specificity for a particular antigen will be coupled to oligonucleotide templates have one specific sequence, even if the specificity between various antibodies in that set varies. The oligonucleotide may be double-stranded or single-stranded. Multiple R-Ab-DNAs may be provided to detect multiple antigens, with each different antibody conjugated to a unique oligonucleotide. Wash buffers are provided in chambers 292*e* through 292*h*. A first-stage PCR master mix, as described above, is provided in chamber 292*i*. A dilution buffer is provided in chamber 292*j*. A second-stage PCR master mix, as described above, is provided in chamber 292*k*. As discussed above, the reagents may be provided dried in chambers 292*b* through 292*l*, and may be rehydrated prior to use via injection of water through seal 239, or each reagent may be provided wet via injection to each individual chamber 292. Combinations thereof are contemplated.

Once the sample and reagents are loaded, the pouch 220 is inserted into the instrument 800. Plunger 268*a* is then depressed and the sample is moved to three-lobed blister 222. Plunger 268*b* is also depressed and the capture antibodies conjugated to magnetic beads (shown as C in FIG. 11) are also moved to three-lobed blister 222. The sample and the C-Ab are mixed via pressure from bladder 828 alternating with pressure from bladders 824, 826. Because mixing is desired, pressure from the bladders 824, 826, 828 may be considerably lower than the pressure used as discussed above for lysis. Illustratively, gentle mixing is obtained. The sample and the C-Ab are allowed to incubate for sufficient time for the capture antibodies to bind to antigens T in the sample (forming C-Ab-T complexes), illustratively for about 5 minutes, although other incubation times may be desirable. For iPCR, it may be desirable to include an additional heater in instrument 800 to maintain incubations at about 37° C.

Once the antigens present in the sample have been sufficiently incubated for capture, the sample is moved to blister 246 and the magnet 850 is deployed, capturing the capture antibodies in blister 246. The unbound portions of the sample are then moved back to three-lobed blister 222, which now functions as a waste reservoir. While magnetic beads are used to restrain the capture antibodies in the examples described herein, it is understood that other capture mechanisms may be used, including solid supports, possibly even cross-linking the capture antibodies to an interior surface of a blister.

If desired, the C-Ab-T complexes may be washed using the pre-wash buffer from chamber 292*c*. Pre-wash buffer is moved into blister 244 via channel 245, the magnet is withdrawn, releasing the C-Ab-T complexes, and the beads are gently moved between blisters 244 and 246. The beads are then recaptured in blister 246 via activation of the magnet 850, and the remaining fluid is moved to three-lobed blister 222. It is expected that this pre-wash may improve discrimination of a positive signal over the background negative signal, but such differences may prove to be insignificant. Additional pre-washes may be performed, if desired.

Plunger 268*d* is depressed and the mixture containing one or more reporter antibodies R-Ab conjugated to oligonucleotide templates (R-Ab-DNA, shown in FIG. 11, Immuno-PCR II scheme, as R with attached nucleic acid) is moved to blister 246. The magnet is retracted and the mixture is gently mixed by moving between blisters 244 and 246. Incubation, illustratively for about 5 minutes although other incubation times may be desirable, allows formation of the ternary complexes C-Ab-T-R-Ab-DNA, as illustrated in FIG. 11, Immuno-PCR II. Activation of the magnet 850 allows capture of the ternary complexes in blister 246, and the remaining fluid is moved to three-lobed blister 222.

Plunger 268*e* is depressed and wash buffer is moved from chamber 292*e* to blister 246. The magnetic bead-ternary complex is washed as in the pre-wash described above, the magnetic bead-ternary complex is recaptured in blister 246, and the remaining fluid is moved to three-lobed blister 222. Washing is repeated multiple times using the wash buffers from chambers 292*f*, 292*g*, and 292*h*, except that mixing is between blisters 246 and 248 to avoid reintroducing unbound R-Ab-DNA complexes that may be residing in blister 244 or channel 243. While four washes are described in this illustrative embodiment, it is understood that any number of washes may be used, illustratively by altering the number of chambers in the fitment 290 or by increasing the volume of the chambers and using only a portion of the wash buffer in a chamber for each wash. It is also understood that removal of all unbound R-Ab-DNA complexes is extremely difficult, even with a large number of washes. Further, for an antigen that is not present in the sample, the presence of just a few molecules of unbound R-Ab-DNA or non-specifically bound R-Ab-DNA complexes specific for that antigen may result in an amplification signal. Thus, while the ideal goal of the washing step is to remove all R-Ab-DNA complexes specific for antigens that are not present in the sample, one illustrative goal is to remove a sufficient number of such R-Ab-DNA complexes such that the amplification curve for that oligonucleotide is delayed and can be distinguished from the amplification curve of a positive sample. Illustratively, more washes should remove more unbound R-Ab- DNA and provide for a lower detection limit, but more washes risk loss of desired ternary complexes through dissociation or loss of magnetic beads not captured by the magnet. After washing is complete, if desired, the captured ternary complex may be heated or enzymatically treated (illustratively with papain, proteinase K, or other suitable enzyme provided via an additional chamber) to release the DNA prior to PCR. Such treatment may improve the first-stage PCR efficiency. It is understood that such treatment may be used with any of the iPCR examples discussed herein.

Once washing is complete, plunger 268i is depressed and the first-stage PCR master mix, as described above, is moved to blister 246. First-stage PCR master mix contains primer pairs for all desired targets. The magnet 850 is released, and optional mixing between blisters 246 and 248 may be used to resuspend the ternary complexes. The mixture is moved to blister 264, where first-stage thermal cycling takes place, as described above. Once the complexed oligonucleotides have been amplified to sufficient levels, as discussed above, the amplified mixture is optionally diluted using the dilution buffer provided in chamber 292j. Some or all of the first-stage amplified mixture may be mixed with the second-stage PCR master mix provided from chamber 292k, and then this mixture is moved to the 18 second-stage blisters 282, where second-stage primers are provided, as discussed above. If desired, one of the second-stage blisters 282 may be used for a negative control, wherein it is known that no antigen is present in the sample, but R-Ab-DNA was provided from chamber 292d and the proper primers are provided in the negative control second-stage blister 282. It is expected that, despite various washes, small amounts of this particular R-Ab-DNA may be present in the first-stage PCR and, accordingly, that small amounts of the first-stage amplified product may be provided to this second-stage blister 282. However, the amounts should be quite small, and the crossing point should be delayed well past that of positive samples. Also, if desired, one of one of the second-stage blisters may be used for a positive control, wherein the sample is spiked with an antigen that is not otherwise being tested (perhaps included with the C-Ab beads), which presumably will bind its corresponding R-Ab-DNA, and which is then amplified in the first-stage PCR. Finally, control blisters 283 are not used in this illustrative embodiment. However, with a minor reconfiguration, blisters 283 may be connected to blister 266 and may provide for six additional second-stage reactions. Alternatively, blisters 283 may be used for other controls, as are desired by the particular application.

As discussed above, because of the difficulty in removing all unbound or non-specifically bound R-Ab-DNA complexes, even negative samples may show some amplification. It is expected that real-time amplification analysis will allow positives to be distinguished from negatives via a difference in cycle number of a threshold crossing point (or an equivalent cycle threshold measurement, such as the cycle number when 50% of amplification is reached).

It is understood that the first-stage multiplex amplification may not be necessary for detection with iPCR, even when testing for multiple antigens. However, the first-stage multiplex amplification may afford more sensitivity.

Example 5: iPCR with iPCR-Specific Pouch

Figure 12:
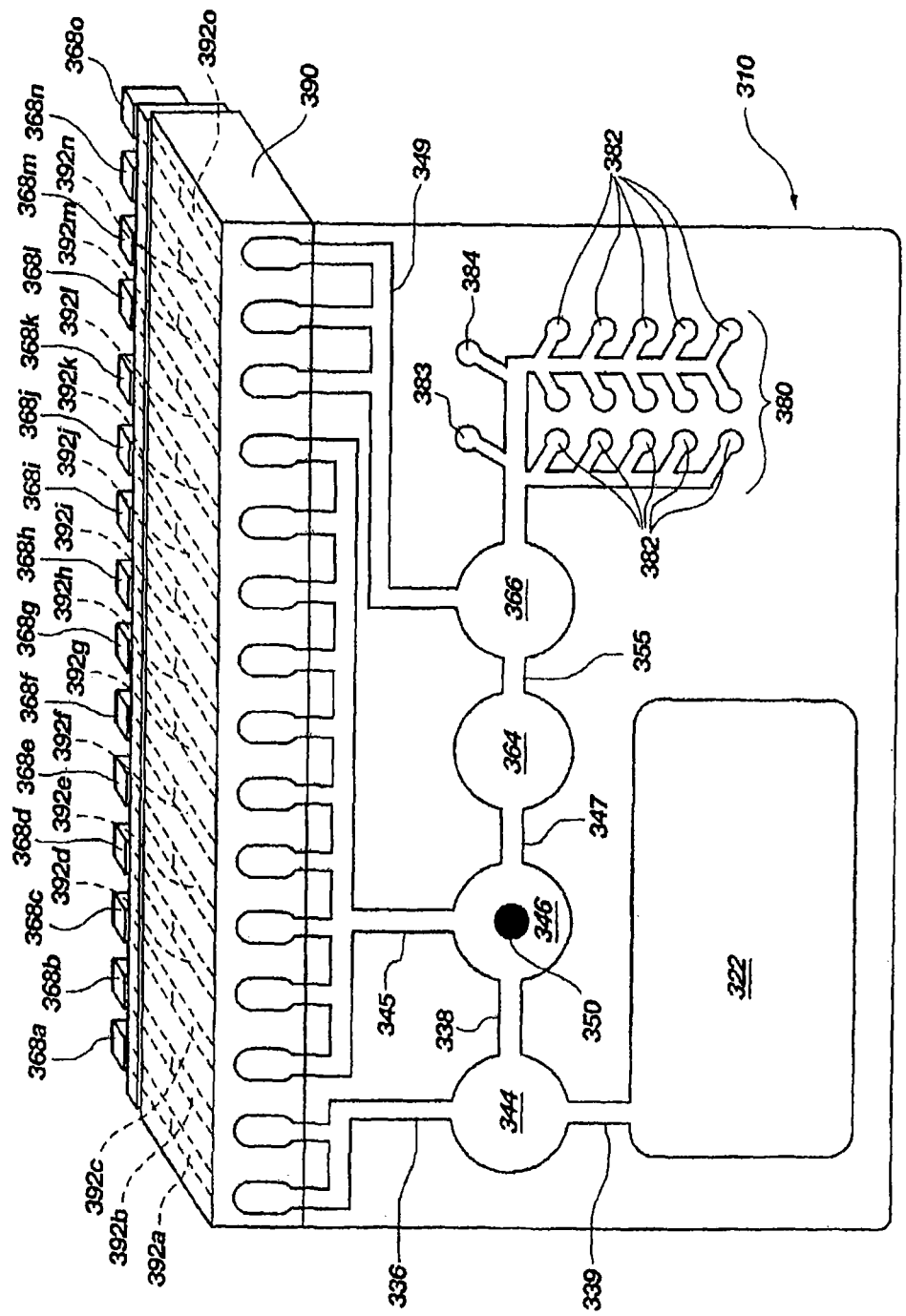
FIG. 12 is similar to FIG. 6, except showing a pouch configured for immuno-PCR.

The above example illustrates a method adapting the pouch 210 of FIG. 6 for iPCR. However, FIG. 12 shows a pouch 310 that is illustratively configured for iPCR. Fitment 390 is similar to fitments 190 and 290, except having 15 chambers 392 and plungers 368. Each chamber 392 (illustratively chamber 392a, where the sample is injected) may have its own injection port, or several chambers may have a connecting channel and may share an injection port (illustratively 392e through 392k, each containing wash buffer). As with the above-described fitments, any combination of injection ports and channels is within the scope of this invention. Pouch 310 differs from pouch 210 of FIG. 6 in one primary way. As cell lysis is usually not needed in iPCR, the three-lobed blister 222 may be replaced by a single large waste reservoir 322. Because multiple washes are desirable in iPCR, waste reservoir 322 is provided with a sufficiently large volume to retain the multiple used buffers, for example 2-5 ml, depending on the application and volume of the reactions. It is understood that instrument 800 may need to be reconfigured somewhat to accommodate pouch 390.

Prior to insertion into the instrument, pouch 390 of FIG. 12 illustratively would have the following components in the chambers 392. The sample to be tested would be injected into chamber 392a. Capture antibodies (C-Ab) conjugated to magnetic beads are provided in chamber 392b. An optional pre-wash buffer is provided in chamber 392c. Reporter antibodies conjugated to their respective oligonucleotide templates (R-Ab-DNA) are provided in chamber 392d. As discussed above, multiple R-Ab-DNAs may be provided to detect multiple antigens, with each different antibody conjugated to a unique oligonucleotide. Wash buffers are provided in chambers 392e through 392k. A first-stage PCR master mix is provided in chamber 392l. A dilution buffer is provided in chambers 392m and 392n. A second-stage PCR master mix is provided in chamber 392o.

To begin, plungers 368a and 368b are depressed, forcing the sample and the capture antibodies C-Ab through channel 343 into blister 344. The sample and the C-Ab are gently mixed, illustratively by moving between blisters 344 and 346 via channel 345, and are incubated as described above. After a sufficient period of time for formation of the C-Ab-T complex, the mixture is moved to blister 346 via channel 338, where a magnet 350 housed in the instrument is deployed, capturing the complexed beads therein. The remaining fluid is moved to waste reservoir 322, via channel 339. Optionally, pre-wash buffer from chamber 392c is moved to blister 346 via channel 345, the magnet 350 is withdrawn, and the magnetic beads are gently washed by moving the fluid between blisters 344 and 346. The magnet 350 is again deployed and the beads are again captured in blister 346.

Next, plunger 368d is depressed moving the reporter antibodies conjugated to nucleic acid template (R-Ab-DNA) to blister 346, the magnet 350 is withdrawn, and the C-Ab-T and the R-Ab-DNA are gently mixed illustratively by moving between blisters 344 and 346 via channel 345 and are incubated as described above. After formation of the ternary complex (C-Ab-T-R-Ab-DNA), the magnet 350 is once again deployed, capturing the ternary complex in blister 346, and the remaining fluid is moved to waste blister 322.

The ternary complex is then washed using the wash buffer from chamber 392e, as described above for the pre-wash. The magnet 350 is again deployed, capturing the ternary complex in blister 346, and the remaining fluid is moved to waste blister 322. Washing is repeated various times, using the wash buffer from chambers 392f through 392k. Thus, in the illustrative embodiment of FIG. 12, seven washes are completed. However, as discussed above, more or fewer washes may be desirable, depending on the particular application.

As illustrated in the Immuno-PCR II scheme shown in FIG. 11, the reporter antibody is conjugated directly to the nucleic acid template. It is understood that the reporter antibody in any of the embodiments discussed herein could be attached to the nucleic acid template by any of a variety of ways, including direct and indirect covalent and non-covalent bonding. Also, the reporter antibody could be attached to the nucleic acid through a variety of mechanisms, including, for example, through the use of secondary antibodies, as illustrated in the Immuno-PCR I scheme of FIG. 11. If secondary antibodies or other indirect coupling mechanisms are used, it may be desirable to add additional ports and further washing steps.

The first-stage PCR master mix, as described above, is then deployed to blister 346 via activation of plunger 368k, and the magnet 350 is once again withdrawn. If gentle mixing is desired, the fluid may be moved between blisters 346 and 364 via channel 347. While mixing can take place between blisters 346 and 344 as before, in the illustrative embodiment mixing takes place between blisters 346 and 364. This aids in reducing the reintroduction of unbound reporter antibody complexes that may be residing in blister 344. The sample is then moved to blister 364. A bladder positioned over 364 is gently pressurized to move blister 364 into contact with a heating/cooling device, such as a Peltier device, and the sample would be thermocycled, as discussed above for first-stage PCR. As discussed above in the previous example, first-stage PCR may be unnecessary with the presently described iPCR, blister 364 and its associated heater may be omitted, and all washes illustratively could take place by mixing between blisters 344 and 346. If first-stage PCR is omitted, the dilution, as discussed below may also be omitted.

Most of the amplified sample is moved to waste blister 322, leaving some amplified sample behind in blister 364 to be diluted. It is understood that if space constraints or other considerations limit the size of blister 322, blisters 344 and 346 may be used to contain the remaining waste. The small amount of remaining amplified sample is mixed with dilution buffer from chamber 392m, which has been moved to blister 366 via channel 349. The sample and the dilution buffer may be mixed gently between blisters 364 and 366, via channel 355. If further dilution is desired, dilution may be repeated using the dilution buffer from chamber 392n. Finally, some of the diluted sample is moved to waste reservoir 322 and the remaining diluted sample is mixed with second-stage PCR master mix from chamber 392o. After mixing, the sample is moved to the various low volume second stage blisters 382, where second-stage primers are provided, as discussed above. In the present configuration, blister 383 may be used for a negative control and blister 384 may be used for a positive control, as discussed above in the previous iPCR example. Second-stage PCR and analysis takes place as described above in the previous iPCR example.

Example 6 Combined PCR and iPCR

In some circumstances, it may be desirable to test for antigens and nucleic acids in one reaction set. For example, a terrorist attack may employ various agents to kill multiple people. In responding to the attack, it may be unknown if the causative agent is a virus, bacterium, or other organism, or if the causative agent is a toxin. The closed-environment system of the pouches of the present invention is well suited for such use. In the embodiment disclosed herein, both PCR and iPCR may take place within a single pouch, allowing for simultaneous detection of various biological and antigenic agents.

FIG. 13 shows a pouch 410 that is similar to pouch 210 of FIG. 6. Illustrative pouch 410 has all of the blisters of pouch 210, but also includes blisters 430, 431, 432, and 433. Pouch 410 also has a larger fitment 490, having twenty chambers 492 with twenty corresponding plungers 468. As above, the fitment could include separate injection ports for each chamber, or various chambers could have connecting channels. Various combinations thereof are within the scope of this invention. The instrument for pouch 410 would be similar to instrument 800, except that additional pneumatic actuators would be needed for blisters 430, 431, 432, and 433 and channels 436, 457, 473, 486, 487, and 488, as well as two additional retractable magnets 451 and 454 adjacent blisters 433 and 431, respectively.

In the illustrative embodiment, the chambers would be loaded as follows. iPCR wash buffer would be provided in chambers 492a through 492e and 492j. The sample to be tested would be injected into chamber 492f. The capture antibodies (C-Ab) conjugated to magnetic beads are provided in chamber 492g. An optional pre-wash buffer is provided in chamber 492h. Reporter antibodies conjugated to their respective oligonucleotide template (R-Ab-DNA) are provided in chamber 492i. A cell lysis buffer is provided in chamber 492k. Nucleic-acid-binding magnetic beads are provided in chamber 492l. Nucleic acid wash buffers are provided in chambers 492m and 492n. A nucleic acid elution buffer is provided in chamber 492o. A first-stage PCR master mix is provided in chamber 492p. A dilution buffer is provided in chambers 492q and 492r. A second-stage PCR master mix is provided in chamber 492s. Controls, as discussed above with respect to FIG. 6, are provided in chamber 492t. It is understood that this arrangement is illustrative and that other configurations are possible. Also, as with the other examples discussed above, one or more of these components may be provided dried in one or more of the blisters of pouch 410.

Once the sample is loaded into chamber 492f and pouch 410 is loaded into the instrument, plungers 468f and 468g are depressed, moving the sample and C-Ab through channel 436 to blister 430. The sample and capture antibodies may be mixed by gently moving them between blisters 430 and 431 and then incubated as described above, to encourage formation of C-Ab-T complexes. The sample is moved to blister 431 and magnet 454 is activated, capturing the C-Ab-T complexes therein. Thus, toxins or other targeted antigens are now captured in blister 431. It is noted that, in the illustrative embodiment, the surface of the magnetic bead portion of the magnetic beads coupled to the capture antibodies is different from the surface of the nucleic-acid-binding magnetic beads, and the magnetic beads coupled to the capture antibodies is illustratively configured not to bind nucleic acids. The remaining fluid is then moved to three-lobed blister 422 via channel 473. This fluid can then be processed and assayed for the presence of target nucleic acids. This division of the sample may be problematic if a targeted antigen is a surface antigen of an organism targeted in the PCR detection. In such a situation, it may be desirable to choose between antigen detection and nucleic acid detection for that organism, or to use separate pouches for PCR and iPCR. Alternatively, the sample may be lysed prior to antibody capture. If lysis would interfere with antibody capture, for example by changing the conformation of the antigen, then the sample may be divided and just a portion of the sample may be lysed prior to antibody capture. If a pre-wash of the C-Ab-T is desired, plunger 468h is activated and the pre-wash buffer from chamber 492h is moved into blister 431. Magnet 454 is withdrawn, the fluid is mixed between blisters 430 and 431, and magnet 454 is once again deployed, capturing the C-Ab-T complex in blister 431. The wash buffer, now possibly containing cells that had been left behind after capture, is moved to three-lobed blister 422, along with the rest of the uncaptured material.

It is understood that the sample is now divided into two parts for separate processing. Antigens present in the sample are now captured in C-Ab-T complexes in blister 431, while cells, viruses, and free nucleic acids present in the sample are now in three-lobed blister 422 awaiting lysis. The two portions of the sample are processed separately until both are ready for first-stage PCR. These processes may take place in any order or simultaneously. However, in the present embodiment, cell lysis must take place prior to substantial processing of the C-Ab-T complexes, so that three-lobed blister may then function as the waste reservoir. If a separate waste reservoir is used, cell lysis can be delayed until after the C-Ab-T complexes have been processed, if desired.

Lysis buffer from chamber 492k is moved into three-lobed blister 422 via channel 436. Bladders adjacent the blisters of three-lobed blister 422 are pressurized as described above with respect to FIG. 6, driving high velocity collisions, shearing the sample, and liberating nucleic acids. Once the cells have been adequately lysed, plunger 468l is activated and nucleic acid binding magnetic beads stored in chamber 492l are injected via channel 436 into three-lobed blister 220. The sample is mixed with the magnetic beads and the mixture is allowed to incubate. The processing then continues as described above with respect to the pouch of FIG. 6. The mixture of sample and beads are forced through channel 438 into blister 444, then through channel 443 and into blister 446, where a retractable magnet 450 captures the magnetic beads from the solution. The un-captured liquid is then forced out of blister 446 and back through blister 444 and into blister 422, which is now used as a waste receptacle. Plunger 468m may be activated to provide a wash solution to blister 444 via channel 445, and then to blister 446 via channel 447. Magnet 450 is retracted and the magnetic beads are washed by moving the beads back and forth from blisters 444 and 446. Once the magnetic beads are washed, the magnetic beads are recaptured in blister 446 by activation of magnet 450, and the wash solution is then moved to blister 422. This process may be repeated using wash reagents in chambers 492n. However, it is understood that more or fewer washes are within the scope of this invention. After washing, elution buffer stored in chamber 492o is moved via channel 447 to blister 448, and the magnet 450 is retracted. The solution is cycled between blisters 446 and 448 via channel 452, breaking up the pellet of magnetic beads in blister 446 and allowing the captured nucleic acids to come into solution. The magnet 450 is once again activated, capturing the magnetic beads in blister 246, and the eluted nucleic acid solution is moved into blister 448.

Returning back to blister 431, the C-Ab-T complexes are therein captured. Plunger 468i is depressed and the reporter antibodies conjugated to nucleic acid template (R-Ab-DNA) are introduced to blister 430, the magnet 454 is withdrawn, and the C-Ab-T and the R-Ab-DNA are gently mixed, illustratively by moving between blisters 430 and 431 via channel 457, and are incubated as described above. After formation of the ternary complex (C-Ab-T-R-Ab-DNA), magnet 454 is once again deployed, capturing the ternary complex in blister 431, and the remaining fluid is moved to blister 422, which is now used as a waste reservoir.

The ternary complex is then washed using the wash buffer from chamber 492j, as described above for the pre-wash. Magnet 454 is again deployed, capturing the ternary complex in blister 446, and the remaining fluid is moved to blister 422. Additional wash buffer from chamber 492a is injected into blister 432 via channel 486, the magnet 454 is withdrawn, and the ternary complex is resuspended by mixing the fluids blisters 431 and 432. The fluids are then moved to blister 433 via channel 487 and the ternary complex is captured therein via activation of magnet 451. The waste fluids are then moved back through blisters 433 and 432 to blister 422. Additional wash buffer is introduced into blister 432 from chamber 492b and washing is repeated by mixing between blisters 432 and 433. Washing is repeated various times using the wash buffer from chambers 492c through 492e. Thus, in the illustrative embodiment of FIG. 13, six washes are completed. However, as discussed above, more or fewer washes may be desirable, depending on the particular application. It is understood that blisters 432 and 433 are used to minimize contamination from prior washes. If desired, blisters 432 and 433 may be omitted and the wash buffers contained in chambers 492a through 492e may be provided directly to either blister 430 or 431, with mixing between blisters 430 and 431.

The washed antibody ternary complex is now captured in blister 433 and the eluted nucleic acids are now in blister 448. It is noted that the antibody ternary complex and the eluted nucleic acids may be processed through PCR in independent reactions, through to separate sets of second-stage PCR blisters. However, in the present embodiment the antibody ternary complex and the eluted nucleic acids are combined for PCR analysis. First-stage PCR master mix, containing all first-stage primers, is injected from chamber 492p into blister 448. The nucleic acid sample is then mixed between blisters 448 and 464 via channel 453. If first-stage PCR is desired for the iPCR components, the nucleic acid sample is then moved to blister 433, magnet 451 is withdrawn, and the re-united sample is illustratively mixed between blisters 433 and 464. The sample is then moved to blister 464, where the sample is thermocycled, as discussed above. Next, the amplified sample may be diluted once or several times, using the dilution buffers from chambers 492q and 492r. Prior to each dilution, a large portion of the amplified sample is removed from blister 464 via either channel 447 or channel 488. With each addition of dilution buffer, the sample is mixed between blisters 464 and 466 via channel 462. After dilution, all or a portion of the sample is mixed with the second-stage PCR master mix from chamber 492s, as described in the examples above.

The sample is then moved from blister 466 via channel 465 to blisters 482 in second-stage amplification zone 480. Blisters 482 each had been previously provided with a primer pair, some of the primer pairs specific for target nucleic acids, while other primer pairs specific for an oligonucleotide conjugated to a reporter antibody. If desired, two blisters 482 may be dedicated to iPCR controls, as discussed above. Blisters 483 may be used for PCR controls, as discussed above with respect to blisters 283 of FIG. 6. While 18 blisters 482 are shown, it is understood that any number of blisters 482 may be used. Second-stage PCR amplification proceeds as discussed above with respect to FIG. 6. It is understood that PCR analysis may use amplification curves, melting curves, or a combination thereof, while iPCR analysis may use crossing thresholds, as discussed above. Other methods of analysis are within the scope of this invention.

REFERENCES

1. Wittwer C T, Fillmore G C, Garling D J. Minimizing the time required for DNA amplification by efficient heat transfer to small samples. Anal Biochem. 1990 May 1; 186(2):328-31.
2. Wittwer C T, Garling D J. Rapid cycle DNA amplification: time and temperature optimization. Biotechniques. 1991 January; 10(1):76-83.
3. Wittwer C T, Herrmann M G, Moss A A, Rasmussen R P. Continuous fluorescence monitoring of rapid cycle DNA amplification. Biotechniques. 1997 January; 22(1):130-1, 134-8.
4. Wittwer C T, Ririe K M, Andrew R V, David D A, Gundry R A, Balis U J. The LightCycler: a microvolume multi-sample fluorimeter with rapid temperature control. Biotechniques. 1997 January; 22(1):176-81
5. Gundry C N, Vandersteen J G, Reed G H, Pryor R J, Chen J, Wittwer C T. Amplicon melting analysis with labeled primers: a closed-tube method for differentiating homozygotes and heterozygotes. Clin Chem. 2003 March; 49(3): 396-406.
6. Wittwer C T, Reed G H, Gundry C N, Vandersteen J G, Pryor R J., High-resolution genotyping by amplicon melting analysis using LCGreen. Clin Chem. 2003 June; 49(6 Pt 1):853-60.0
7. McKinney J T, Longo N, Hahn S, Matern D, Rinaldo P, Dobrowolski S F. Comprehensive analysis of the human medium chain acyl-CoA dehydrogenase gene. Mol Gen Metab. In press
8. Dobrowolski S F, Amat di San Filippo C, McKinney J T, Wilcken B, Longo N Identification of novel mutations in the SLC22A5 gene in primary carnitine deficiency with dye-binding/high-resolution thermal denaturation, Human Mutation, submitted
9. McKinney J T, Saunders C, Dobrowolski S F, High-resolution melting analysis of the human galactose-1-phosphate uridyl transferase gene, in preparation
10. http://www.defenselink.mil/contracts/2003/ct20030925.html
11. Poritz M A, Abbott R, Gerber T, Thatcher S, Bird A, Tuck A, Newswander A M, Belisle S, Ririe K, A Handheld, Battery-operated Real-time PCR Machine, American Society for Microbiology Annual Meeting, Baltimore MD, Mar. 9-12, 2003
12. Elnifro E M, Ashshi A M, Cooper R J, Klapper P E. Multiplex PCR: optimization and application in diagnostic virology. Clin Microbiol Rev. 2000 October; 13(4): 559-70. Review.
13. Elnifro E M, Cooper R J, Klapper P E, Yeo A C, Tullo A B. Multiplex polymerase chain reaction for diagnosis of viral and chlamydial keratoconjunctivitis. Invest Ophthalmol Vis Sci. 2000 June; 41(7):1818-22.
14. Giaever, G., et al. Genomic profiling of drug sensitivities via induced haploinsufficiency. Nature Genetics. 1999, 21, 278-283
15. Winzeler, E., et al Functional Characterization of the *Saccharomyces cerevisiae* Genome by Gene Deletion and Parallel Analysis. Science. 1999. 285, 901-906.
16. Sano, T., C. L. Smith, and C. R. Cantor, Immuno-PCR: very sensitive antigen detection by means of specific antibody-DNA conjugates. Science, 1992. 258(5079): p. 120-2.
17. Niemeyer, C. M., M. Adler, and R. Wacker, Immuno-PCR: high sensitivity detection of proteins by nucleic acid amplification. Trends Biotechnol, 2005. 23(4): p. 208-16.
18. Adler, M., Immuno-PCR as a clinical laboratory tool. Adv Clin Chem, 2005. 39: p. 239-92.
19. Barletta, J. M., et al., Detection of ultra-low levels of pathologic prion protein in scrapie infected hamster brain homogenates using real-time immuno-PCR. J Virol Methods, 2005. 127(2): p. 154-64.
20. Adler, M., et al., Detection of Rotavirus from stool samples using a standardized immuno-PCR ("Imperacer") method with end-point and real-time detection. Biochem Biophys Res Commun, 2005. 333(4): p. 1289-94.
21. Lind, K. and M. Kubista, Development and evaluation of three real-time immuno-PCR assemblages for quantification of PSA. J Immunol Methods, 2005.304(1-2): p. 107-16.
22. Schiavo, S., et al., Comparison of fluorometric detection methods for quantitative polymerase chain reaction (PCR). J Immunoassay Immunochem, 2005. 26(1): p. 1-12.
23. Barletta, J. M., D. C. Edelman, and N. T. Constantine, Lowering the detection limits of HIV-1 viral load using real-time immuno-PCR for HIV-1 p24 antigen. Am J Clin Pathol, 2004. 122(1): p. 20-7.
24. McKie, A., et al., A quantitative immuno-PCR assay for the detection of mumps-specific IgG. J Immunol Methods, 2002.270(1): p. 135-41.
25. Chao, H. Y., et al., A highly sensitive immuno-polymerase chain reaction assay for *Clostridium botulinum* neurotoxin type A. Toxicon, 2004. 43(1): p. 27-34.
26. Wu, H. C., et al., Detection of *Clostridium botulinum* neurotoxin type A using immuno-PCR. Lett Appl Microbiol, 2001. 32(5): p. 321-5.
27. Liang, H., et al., A highly sensitive immuno-PCR assay for detecting Group A *Streptococcus*. J Immunol Methods, 2003. 279(1-2): p. 101-10.
28. Adler, M., R. Wacker, and C. M. Niemeyer, A real-time immuno-PCR assay for routine ultrasensitive quantification of proteins. Biochem Biophys Res Commun, 2003. 308(2): p. 240-50.
29. Allen, R. C., et al., An immuno-PCR method for detecting *Bacillus thuringiensis* Cry1Ac toxin. J Immunol Methods, 2006. 308(1-2): p. 109-15.
30. Hendrickson, E. R., et al., High sensitivity multianalyte immunoassay using covalent DNA-labeled antibodies and polymerase chain reaction. Nucleic Acids Res, 1995 23(3): p. 522-9.
31. Joerger, R. D., et al., Analyte detection with DNA-labeled antibodies and polymerase chain reaction. Clin Chem, 1995. 41(9): p. 1371-7.
32. Hujer, et. al., Multi-drug Resistant *Acinetobacter* spp. Isolates from Military and Civilian Patients Treated at the Walter Reed Army Medical Center: Analysis of Antibiotic Resistance Genes. Antimicrob Agents Chemother. 2006 Sep. 25.
33. Sanchez et al., A multiplex assay with 52 single nucleotide polymorphisms for human identification. Electrophoresis. 2006 v27 p. 1713-24.
34. Zhou et al., Closed-tube genotyping with unlabeled oligonucleotide probes and a saturating DNA dye. Clin Chem. 2004 50 p. 1328-35.

While references are made herein to PCR and iPCR, it is understood that the devices and methods disclosed herein may be suitable for use with other nucleic acid amplification or other biological processing methods, as are known in the art, particularly methods that benefit from a first-stage multiplex reaction and a second-stage individual reaction. Illustrative non-limiting second-stage reactions include primer extension, including allele-specific primer extension; extension terminations, including termination by incorporation of one or more dideoxy nucleotides; incorporation of fluorescent or non-fluorescent labels; and other enzymatic reactions requiring a change in reaction mixture components or component ratios, such as asymmetric PCR, allele-specific PCR, invader assays, and other isothermal amplification or detection chemistries.

Although the invention has been described in detail with reference to preferred embodiments, variations and modifications exist within the scope and spirit of the invention as described and defined in the following claims.

The invention claimed is:

1. A method of nucleic acid extraction and multiplex PCR in a self-contained system, comprising:
   (a) providing the self-contained system having, in fluid communication:
      i. one or more ports, including an injector port for introducing the sample into the self-contained system,
      ii. a nucleic acid preparation zone, the nucleic acid preparation zone configured for purifying nucleic acids,
      iii. at least one amplification zone, the amplification zone configured for amplification of the plurality of nucleic acids that may be in the sample;
   (b) introducing the sample into the self-contained system via the injector port, and closing the injector port subsequent to introducing the sample into the self-contained system;
   (c) preparing the nucleic acids in the nucleic acid preparation zone, and moving the nucleic acids into the amplification zone;
   (d) mixing the nucleic acids in the sample with PCR reaction components including a plurality of primer pairs configured for amplifying the targets,
   (e) thermal cycling the nucleic acids in the amplification zone to create an amplification mixture, wherein mixing continues during thermal cycling, and
   (f) detecting which of the plurality of nucleic acids are present in the amplification mixture.

2. The method of claim 1, wherein the ports are sealable ports that provide the only access from an exterior of the container such that when all of the one or more sealable ports are closed, the container is fully closed, the method comprising (g) closing the sealable ports, wherein step (g) takes place after step (b).

3. The method of claim 1, wherein at least one of the ports is a one-way valve.

4. The method of claim 1 wherein the container further comprises a cell lysis zone configured for lysing cells or spores located in the sample, wherein the nucleic acid preparation zone is fluidly connected to the injector port through the cell lysis zone, and further comprising the step of lysing cells or spores, wherein the lysing step occurs in the cell lysis zone prior to step (c).

5. The method of claim 1, wherein the amplification zone is provided with dried amplification reagents therein.

6. The method of claim 1, wherein the thermal cycling step is performed by a heater that repeated thermal cycles the nucleic acids between a denaturation temperature and an annealing temperature.

7. The method of claim 1, wherein the thermal cycling step is performed by repeatedly moving the nucleic acids between a first heater set at a denaturation temperature and a second heater set at an annealing temperature.

8. The method of claim 1, further comprising dividing the nucleic acids into a plurality of individual reaction sites prior to step (d).

9. The method of claim 1, further comprising a second-stage PCR reaction further comprising subsequent to step (d), dividing the nucleic acids into a plurality of individual reaction sites and further amplifying the nucleic acids.

10. The method of claim 9, wherein the nucleic acids are heated prior to the dividing step to provide benefits of hot-start amplification.

* * * * *

UNITED STATES PATENT AND TRADEMARK OFFICE
CERTIFICATE OF CORRECTION

PATENT NO. : 11,866,774 B2
APPLICATION NO. : 17/114622
DATED : January 9, 2024
INVENTOR(S) : Ririe et al.

It is certified that error appears in the above-identified patent and that said Letters Patent is hereby corrected as shown below:

In the Specification

Column 4, Line 55: Please correct "(ICAM)" to read --(ICAN)--

Column 28, Line 8: Please correct "5151" to read --515$I$--

Column 33, Line 49: Please correct "1×LC Green" to read --1XLC Green®--

Column 34, Line 2: Please correct "Sc" to read --Sc1--

Column 36, Line 13: Please correct "5.0×10-$^{19}$" to read --5.0 × 10-$^{19}$--

Column 38, Line 55: Please correct "102 to 1" to read --$10^2$ to $10^3$--

Column 47, Line 30: Please correct "853-60.0." to read --853-60.--

Signed and Sealed this
Thirtieth Day of April, 2024

Katherine Kelly Vidal
*Director of the United States Patent and Trademark Office*